(12) United States Patent
Eberwine et al.

(10) Patent No.: US 9,114,159 B2
(45) Date of Patent: Aug. 25, 2015

(54) TRANSCRIPTION FACTORS IN NEURONAL DENDRITES-DENDRITIC PROTEIN SYNTHESIS AND CELL DEATH

(75) Inventors: James H. Eberwine, Philadelphia, PA (US); Lindy E. Barrett, New York, NY (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1609 days.

(21) Appl. No.: 11/990,376

(22) PCT Filed: Aug. 17, 2006

(86) PCT No.: PCT/US2006/032513
§ 371 (c)(1),
(2), (4) Date: Apr. 16, 2009

(87) PCT Pub. No.: WO2007/022478
PCT Pub. Date: Feb. 22, 2007

(65) Prior Publication Data
US 2009/0227531 A1    Sep. 10, 2009

Related U.S. Application Data

(60) Provisional application No. 60/708,981, filed on Aug. 17, 2005, provisional application No. 60/736,993, filed on Nov. 15, 2005.

(51) Int. Cl.
| | | |
|---|---|---|
| *C12N 15/11* | (2006.01) | |
| *C12N 13/00* | (2006.01) | |
| *C12Q 1/28* | (2006.01) | |
| *C12N 5/00* | (2006.01) | |
| *A61K 48/00* | (2006.01) | |
| *A61K 38/17* | (2006.01) | |

(52) U.S. Cl.
CPC ........... *A61K 48/005* (2013.01); *A61K 38/1709* (2013.01)

(58) Field of Classification Search
None
See application file for complete search history.

(56) References Cited

U.S. PATENT DOCUMENTS

2003/0229003 A1*  12/2003  Oettgen et al. .............. 514/1

OTHER PUBLICATIONS

Salinas et al., 2004, J. Cell Biol. 165:767-773.*
Mao et al., 2003, J. Neurochem, 85:1006-1017.*
Barrett et al., "Elk-1 associates with the mitochondrial permeability transition pore complex in neurons", PNAS, 103(13): 5155-5160 (2006).
Beutner et al., "Complexes between porin, hexokinase, mitochondrial creatine kinase and adenylate translocator display properties of the permeability transition pore. Implication for regulation of permeability transition by the kinases", Biochimica et Biophysica Acta 1368: 7-18 (1998).
Chai et al., "c-Fos oncogene regulator Elk-1 interacts with BRCA1 splice variants BRCA1a/1b and enhances BRCA1a/1b-mediated growth suppression in breast cancer cells", Oncogene, 20: 1357-1367 (2001).
Crino et al., "Molecular Characterization of the Dendritic Growth Cone: Regulated mRNA Transport and Local Protein Synthesis", Neuron, 17: 1173-1187 (1996).
Davis et al., "The MAPK/ERK Cascade Targets Both Elk-1 and cAMP Response Element-Binding Protein to Control Long-Term Potentiation-Dependent Gene Expression in the Dentate Gyrus In Vivo", The Journal of Neuroscience, 20(12): 4563-4572 (2000).
Eberwine et al., "Local translation of classes of mRNAs that are targeted to neuronal dendrites", PNAS, 98(13): 7080-7085 (2001).
Halestrap et al., "The permeability transition pore complex: another view", Biochimie 84: 153-166 (2002).
Janknecht et al., "Elk-1 protein domains required for direct and SRF-assisted DNA-binding", Nucleic Acids Research, 20(13): 3317-3324 (1992).
Jiang et al., "Zn2 Induces Permeability Transition Pore Openings and Release of Pro-apoptotic Peptides from Neuronal Mitochondria", The Journal of Biological Chemistry, 276(50): 47524-47529 (2001).
Job et al., "Identification of sites for exponential translation in living dendrites", PNAS, 98(23): 13037-13042 (2001).
Kacharmina et al., "Stimulation of glutamate receptor protein synthesis and membrane insertion within isolated neuronal dendrites", PNAS, 97(21): 11545-11550 (2000).
Kleiman et al., "Inhibition of protein synthesis alters the subcellular distribution of mRNA in neurons but does not prevent dendritic transport of RNA", Proc. Natl. Acad. Sci. USA, 90: 11192-11196 (1993).
Mao et al., "The Scaffold Protein Homer1b/c Links Metabotropic Glutamate Receptor 5 to Extracellular Signal-Regulated Protein Kinase Cascades in Neurons", The Journal of Neuroscience, 25(10): 2741-2752 (2005).
Pastorcic et al., "ETS transcription factors ER81 and Elk1 regulate the transcription of the human presenilin 1 gene promoter", Molecular Brain Research 113: 57-66 (2003).
Peterson et al., "Photoporation and cell transfection using a violet diode laser", Optics Express, 13(2): 595-600 (2005).
Sgambato et al., "In Vivo Expression and Regulation of Elk-1, a Target of the Extracellular-Regulated Kinase Signaling Pathway, in the Adult Rat Brain", The Journal of Neuroscience, 18(1): 214-226 (1998).
Andrew D. Sharrocks, "The ETS-Domain Transcription Factor Family", Molecular Cell Biology, 2: 827-837 (2001).

(Continued)

*Primary Examiner* — Christopher M Babic
*Assistant Examiner* — Kelaginamane T Hiriyanna
(74) *Attorney, Agent, or Firm* — Riverside Law LLP

(57) ABSTRACT

The present invention relates to methods of altering the competence of a dendrite and/or the viability of a neuron by modulating the level of Elk-1 in a dendrite. The present invention also provides methods of altering the ATP levels in a neuron, methods of isolating at least one protein of a mitochondrial permeability transition pore complex, methods of introducing an RNA into a neuron, methods of translating an RNA in a dendrite, methods of monitoring risk of neurodegeneration of a neuron, and methods of treatment for neurodegenerative diseases.

3 Claims, 15 Drawing Sheets

(56) References Cited

OTHER PUBLICATIONS

Andrew D. Sharrocks, "Complexities in ETS-Domain Transcription Factor Function and Regulation: Lessons from the TCF (Ternary Complex Factor) Subfamily", Biochemical Society, 1-9 (2002).

Sugimoto et al., "The Calcium/Calmodulin-dependent Protein Phosphatase Calcineurin Is the Major Elk-1 Phosphatase", The Journal of Biological Chemistry, 272 (47): 29415-29418 (1997).

Tang et al., "Disturbed Ca2+ signaling and apoptosis of medium spiny neurons in Huntington's disease", PNAS, 102(7): 2602-2607 (2005).

Thiels et al, "Long-Term Depression in the Adult Hippocampus In Vivo Involves Activation of Extracellular Signal-Regulated Kinase and Phosphorylation of Elk-1", The Journal of Neuroscience, 22(6): 2054-2062 (2002).

Vanhoutte et al., "Opposing Roles of Elk-1 and Its Brain-specific Isoform, Short Elk-1, in Nerve Growth Factor-induced PC12 Differentiation", The Journal of Biological Chemistry, 276(7): 5189-5196 (2001).

Wang et al., "The Spry Domain-containing SOCS Box Protein 1 (SSB-1) Interacts with MET and Enhances the Hepatocyte Growth Factor-induced Erk-Elk-1 Serum Response Element Pathway", The Journal of Biological Chemistry, 280(16): 16393-16401 (2005).

Yang et al., "Dynamic Interplay of the SUMO and ERK Pathways in Regulating Elk-1 Transcriptional Activity", Molecular Cell, 12: 63-74 (2003).

\* cited by examiner

Figure 3A

|  |  | SN (H-160) | SN (I-20) | WB (H-160) | MT (H-160) |
|---|---|---|---|---|---|
| ANT (adenine nucleotide transporter) | Inner mitochondrial membrance pore; ATP/ADP exchange | √ |  | √ |  |
| HXK (hexokinase) | Catalyzes first step in glucose metabolism; binds to VDAC1 | √ | √ | √ | √ |
| VDAC1 (voltage dependent anion channel) | Outer mitochondrial membrane port; voltage-sensitive | √ |  | √ |  |
| uMTCK (ubiquitous mitochondrial creatine kinase) | Synthesis of phosphocreatine | √ |  | √ | √ |

SEQUENCE LISTING

<160> NUMBER OF SEQ ID NOS: 8

<210> SEQ ID NO 1
<211> LENGTH: 1314
<212> TYPE: DNA
<213> ORGANISM: Rattus norvegicus

<400> SEQUENCE: 1

| | | | | | |
|---|---|---|---|---|---|
| atggacccat | ctgtgacact | gtggcagttt | ctgctgcagc | ttctaagaga | acaaggtaat | 60 |
| ggccacatca | tctcctggac | ctcacgggat | ggtggtgagt | tcaagttggt | ggatgcagaa | 120 |
| gaggtggccc | ggctatgggg | actgcgcaag | aacaagacca | catgaatta | tgacaagctt | 180 |
| agccgggcct | tgcgctacta | ctatgataag | aatatcatcc | gcaaggtgag | cggccagaag | 240 |
| tttgtctaca | agtttgtgtc | ctacccagag | gttgcagggt | gctccactga | agactgccca | 300 |
| ccccagcctg | aggtgtctgt | aacctcggcc | gtagcaatgg | ccctgctac | tgtccattca | 360 |
| ggcccagggg | acaatgccac | tggaaagcca | ggaacaccaa | agggtgcagg | aatgacaggc | 420 |
| caaggtggct | tagcacgaag | cagccggaat | gaatacatgc | gctcgggcct | ctattctacc | 480 |
| ttcacaatac | agtccctgca | gccacagcca | cccttcatc | ctcggcctgc | ctcagtgctt | 540 |
| cccaacacta | cccctgcagg | agtaccagca | cccccctcag | ggagcaggag | caccagtcca | 600 |
| aaccccttag | aagcctgctt | ggaggcagaa | gaggctggtc | tgcccctgca | ggttatctta | 660 |
| accccaccag | aggcccaaa | ccagaaatct | gaagagttga | gtctgaaccc | aggttttggc | 720 |
| cgtccacaac | cccagaagt | caagtggag | gggcctaagg | aagaattgga | agttacagag | 780 |
| gttggaggct | tcagtccaga | agctgtcaaa | gctgaacaag | aagtctcacc | ctcagaaggc | 840 |
| ctgctggctc | ggctcccagc | catcctaaca | gagaatacag | cacaggtgtg | tggcctctcc | 900 |
| acctccacca | ctgagatcac | ccaaccccag | aagggccgga | agccccgaga | cctggaactt | 960 |
| ccacttagcc | caagcctgct | aggtggccaa | ggacccgaac | ggactccagg | atcaggaaca | 1020 |
| agctctggtc | ttcaggcaca | ggggccagca | ctaacaccat | ccttgctccc | cacacatacc | 1080 |
| ttgaccccgg | tgctgctgac | acccagctcg | ctgccccca | gcatccattt | ctggagcact | 1140 |
| ctgagtccaa | ttgcaccgcg | tagtccagcc | aagctctcct | tccaggtagg | attccctagc | 1200 |
| cctgtgttgg | aaatgtttcc | gtccagtggc | agcgcacagg | tgcacatccc | ttccatcagc | 1260 |
| gtggatggcc | tctcgactcc | cgtggtgctc | tccccagggc | cccaaaagcc | atga | 1314 |

<210> SEQ ID NO 2
<211> LENGTH: 2828
<212> TYPE: DNA
<213> ORGANISM: Homo sapiens
<220> FEATURE:
<221> NAME/KEY: misc_feature
<222> LOCATION: (234)..(1520)
<223> OTHER INFORMATION: coding sequence

<400> SEQUENCE: 2

| | | | | | |
|---|---|---|---|---|---|
| acattgggct | cctcctcctc | gggcccacgt | gagctgtagg | gaaacgcagg | ggcggcttct | 60 |
| aggtgctgcc | gccgccaccg | ccaccaccac | ctccaccgcc | gcctcggaac | ccaggcctgg | 120 |
| ggggcggtgg | ggccgcgtat | ggagcccccg | cccccggag | ctgccaacat | tgccaacgcc | 180 |
| accgccacgc | tacacacagg | taccctggg | atggcgtgag | cactcccca | gcgatggacc | 240 |
| catctgtgac | gctgtggcag | tttctgctgc | agctgctgag | agagcaaggc | aatggccaca | 300 |
| tcatctcctg | gacttcacgg | gatggtgtg | aattcaagct | ggtggatgca | gaggaggtgg | 360 |
| cccggctgtg | gggactacgc | aagaacaaga | ccaacatgaa | ttacgacaag | ctcagccggg | 420 |

```
ccttgcggta ctactatgac aagaacatca tccgcaaggt gagcggccag aagttcgtct    480
acaagtttgt gtcctaccct gaggtcgcag ggtgctccac tgaggactgc ccgccccagc    540
cagaggtgtc tgttacctcc accatgccaa atgtggcccc tgctgctata catgccgccc    600
caggggacac tgtctctgga aagccaggca cacccaaggg tgcaggaatg caggcccag     660 gcggtttggc acgcagcagc cggaacgagt acatgcgctc gggcctctat tccaccttca    720
ccatccagtc tctgcagccg cagccacccc ctcatcctcg gcctgctgtg gtgctcccca    780
atgcagctcc tgcaggggca gcagcgcccc cctcggggag caggagcacc agtccaagcc    840
ccttggaggc ctgtctggag gctgaagagg ccggcttgcc tctgcaggtc atcctgaccc    900
cgcccgaggc cccaaacctg aaatcggaag agcttaatgt ggagccgggt ttgggccggg    960 cttt gccccc agaagtgaaa gtagaagggc ccaaggaaga gttggaagtt gcgggggaga   1020
gagggtttgt gccagaaacc accaaggccg agccagaagt ccctccacag gagggcgtgc   1080
cagcccggct gcccgcggtt gttatggaca ccgcagggca ggcgggcggc catgcggctt   1140
ccagccctga gatctcccag ccgcagaagg gccggaagcc ccgggaccta gagcttccac   1200
tcagcccgag cctgctaggt gggccgggac ccgaacggac cccaggatcg ggaagtggct   1260
ccggcctcca ggctccgggg ccggcgctga ccccatccct gcttcctacg catacattga   1320
ccccggtgct gctgacaccc agctcgctgc ctcctagcat tcacttctgg agcaccctga   1380
gtcccattgc gccccgtagc ccggccaagc tctccttcca gtttccatcc agtggcagcg   1440
cccaggtgca catcccttct atcagcgtgg atggcctctc gaccccgtg gtgctctccc    1500 cagggcccca gaagccatga ctactaccac caccaccacc ccccttctg gggtcactcc     1560 atccatgctc tctccagcca gccatctcaa ggagaaacat agttcaactg aaagactcat    1620
gctctgattg tggtggggtg gggatccttg ggaagaatta ctcccaagag taactctcat    1680
tatctcctcc acagaaaaca cacagcttcc acaacttctc tgttttctgt cagtccccca    1740
gtggccgccc ttacacgtct cctacttcaa tggtaggggc ggtttattta tttatttttt    1800
gaaggccact gggaggagcc tgacctaacc ttttagggtg gttaggacat ctcccccacc    1860
tccccacttt tttcccccaag acaagacaat cgaggtctgg cttgagaacg acctttcttt   1920
ctttatttct cagcctgccc ttggggagat gagggagccc tgtctgcgtt tttggatgtg    1980
agtagaagag ttagtttgtt ttgttttatt attcctggcc atactcaggg gtccaggaag    2040
aatttgtacc atttaatggg ttgggagtct tggccaagga agaatcacac ccttggaata    2100
gaaatttcca cctcccccaa cctttctctc agacagctta tccttttttca accaactttt   2160 tggccaggga ggaatgtccc ttttgttctt cccctgaga agccattcct ttgtctgcca     2220
acctccctgg ggtcctgcct gtttcctccc aatggagggt tttttggg ggtggtcccc      2280 gtctgggggg ccctccagc cagtactcca ggtctccctg tctctccccc gctgccattt     2340
tgatagtata atctatttt aaatgggggct tttcaatagg ggagagggag tcatctcttc    2400
ctatatttgg tggggtgggt gggaaggaag ggatttgggg gggaatcttc tgcctcctcc    2460
ccactccaag tgtttatttt tgataccaaa catgaattt cagttccctc cctcccagcc     2520
ccccaatttc ctgcgggcgg gtacaaagga ccctttcaat gtccctggag ttgggaggga    2580
ggaatggggg acataaagcc tgtcctgtct ctattctagg caagagagag tgggttcaaa    2640
agactcctgg gctcacctgt tagcgctggc ccagcccagg ccttgggacc tggggggttgg   2700 tgatttgggg gacagtgcta cactcgtctc cactgtttgt tttacttccc caaaatggac    2760
```

```
ctttttttttt tctaaagagt cccagagaat ggggaattgt tcctgtaaat atatatttttt    2820 caaagtga                                                               2828

<210> SEQ ID NO 3
<211> LENGTH: 1655
<212> TYPE: DNA
<213> ORGANISM: Mus musculus
<220> FEATURE:
<221> NAME/KEY: misc_feature
<222> LOCATION: (188)..(1477)
<223> OTHER INFORMATION: coding sequence

<400> SEQUENCE: 3
aagaggtaat cccaggggcg gcttctggtt gctgcttctg ctgtcgccgc caccaccgcc      60
gccgccttgg aaccggggcc tggggacgg tggggcctcg tatggagccc ccgcccccccg     120 gagctgccac tgccaccgcc gcgccactcg caggtactcc tggaatggcg tgagtgcttc     180
cctagtgatg gacccatctg tgacgctgtg gcagtttctg ctgcagcttc tgagagaaca     240
aggtaatggc cacatcatct cctggacctc acgggatggg ggtgagttca agttggtgga     300
tgcagaggag gtggcccggc tatggggact gcgcaagaac aagaccaaca tgaattacga     360
caagcttagc cgggccttgc ggtactacta tgataagaat atcatccgca aggtgagcgg     420
ccagaagttt gtctacaagt ttgtgtccta cccagaggtt gcagggtgct ccactgaaga     480
ctgcccaccc cagcctgagg tgtctgtaac ctcggccata gccatggccc tgctactgc      540 ccatgcaggc caggggaca cggccactgg aaagccagga acaccaaagg gtgcaggaat      600
gacaggccaa ggtggcttag cacgaagcag ccggaatgaa tacatgcgct cgggcctcta     660
ttctaccttc acaatacaat ccctgcagcc acagccacag ccacccattc ctcctcggcc     720
tgcctcagtg cttcccaaca ctaccccctgc aggagtacca gcacccgcct cagggagcag     780
gagcaccagt ccaaacccct tagaagcctg tttggaagca gaagaggctg gtctgcccct     840
gcaggttatc ctaaccccac cagaggcccc aaaccagaaa tccgaagagt tgagtctgga     900
cccaagtttt ggccatccac agcccccaga agtcaaagtg gaggggccta aggaagaatt     960
ggaagctgca agggctggag gcttcagttc agaagctgtc aaagctgaac cagaagtctc    1020
agcctcagaa ggtctgctgg ctcggctccc agccatccta acagagaaca cagcccaggt    1080
gtgtggcctc tccacttcca ccactgagat caccaaccg cagaagggcc gaaagcctcg     1140
ggacctggaa cttccactta gcccaagcct gctgggtggc cagggacctg aacggactcc    1200
aggatcagga acaagctctg gtcttcaggc accggggcca gcgctaacgc catcccctgct    1260 cccccacacat accttgaccc cggtgctgct gacacccagc tcgctgcccc ctagcatcca    1320
tttctggagc actctgagtc caattgcacc ccgtagtcca gccaagctct ccttccagtt    1380
tccgtccagt ggcagcgcac aggtgcacat cccttccatc agtgtggatg gcctctcgac    1440
ccccgtggtg ctctccccag ggccccagaa gccatgacta ccaccaccac ccctttttg     1500 gagtccatcc atctatgctc ctgaactctc cagttagcca tctcaaggag aaacatagtt    1560
aaactgacag acttaagctc tgattgtggt ggggtggata ttcctggaaa agtgaatatt    1620
tcactaactc ctccacccaa aaaaaaaaaa aaaaa                                1655

<210> SEQ ID NO 4
<211> LENGTH: 19
<212> TYPE: DNA
<213> ORGANISM: Artificial sequence
<220> FEATURE:
<223> OTHER INFORMATION: chemically synthesized
```

-continued

<400> SEQUENCE: 4
ggtgagcggc cagaagttt                                                      19

<210> SEQ ID NO 5
<211> LENGTH: 19
<212> TYPE: DNA
<213> ORGANISM: Artificial sequence
<220> FEATURE:
<223> OTHER INFORMATION: chemically synthesized

<400> SEQUENCE: 5
agttggtgga tgcagagga                                                      19

<210> SEQ ID NO 6
<211> LENGTH: 437
<212> TYPE: PRT
<213> ORGANISM: Rattus norvegicus

<400> SEQUENCE: 6

Met Asp Pro Ser Val Thr Leu Trp Gln Phe Leu Leu Gln Leu Leu Arg
1               5                   10                  15

Glu Gln Gly Asn Gly His Ile Ile Ser Trp Thr Ser Arg Asp Gly Gly
            20                  25                  30

Glu Phe Lys Leu Val Asp Ala Glu Val Ala Arg Leu Trp Gly Leu
        35                  40                  45

Arg Lys Asn Lys Thr Asn Met Asn Tyr Asp Lys Leu Ser Arg Ala Leu
    50                  55                  60

Arg Tyr Tyr Tyr Asp Lys Asn Ile Ile Arg Lys Val Ser Gly Gln Lys
65                  70                  75                  80

Phe Val Tyr Lys Phe Val Ser Tyr Pro Glu Val Ala Gly Cys Ser Thr
                85                  90                  95

Glu Asp Cys Pro Pro Gln Pro Glu Val Ser Val Thr Ser Ala Val Ala
            100                 105                 110

Met Ala Pro Ala Thr Val His Ser Gly Pro Gly Asp Asn Ala Thr Gly
        115                 120                 125

Lys Pro Gly Thr Pro Lys Gly Ala Gly Met Thr Gly Gln Gly Gly Leu
    130                 135                 140

Ala Arg Ser Ser Arg Asn Glu Tyr Met Arg Ser Gly Leu Tyr Ser Thr
145                 150                 155                 160

Phe Thr Ile Gln Ser Leu Gln Pro Gln Pro Leu His Pro Arg Pro
                165                 170                 175

Ala Ser Val Leu Pro Asn Thr Thr Pro Ala Gly Val Pro Ala Pro Pro
            180                 185                 190

Ser Gly Ser Arg Ser Thr Ser Pro Asn Pro Leu Glu Ala Cys Leu Glu
        195                 200                 205

Ala Glu Glu Ala Gly Leu Pro Leu Gln Val Ile Leu Thr Pro Pro Glu
    210                 215                 220

Ala Pro Asn Gln Lys Ser Glu Glu Leu Ser Leu Asn Pro Gly Phe Gly
225                 230                 235                 240

Arg Pro Gln Pro Pro Glu Val Lys Val Glu Gly Pro Lys Glu Glu Leu
                245                 250                 255

Glu Val Thr Glu Val Gly Gly Phe Ser Pro Glu Ala Val Lys Ala Glu
            260                 265                 270

Gln Glu Val Ser Pro Ser Glu Gly Leu Leu Ala Arg Leu Pro Ala Ile
        275                 280                 285

```
Leu Thr Glu Asn Thr Ala Gln Val Cys Gly Leu Ser Thr Ser Thr Thr
290                 295                 300

Glu Ile Thr Gln Pro Gln Lys Gly Arg Lys Pro Arg Asp Leu Glu Leu
305                 310                 315                 320

Pro Leu Ser Pro Ser Leu Leu Gly Gly Gln Gly Pro Glu Arg Thr Pro
                325                 330                 335

Gly Ser Gly Thr Ser Ser Gly Leu Gln Ala Gln Gly Pro Ala Leu Thr
                340                 345                 350

Pro Ser Leu Leu Pro Thr His Thr Leu Thr Pro Val Leu Leu Thr Pro
                355                 360                 365

Ser Ser Leu Pro Pro Ser Ile His Phe Trp Ser Thr Leu Ser Pro Ile
370                 375                 380

Ala Pro Arg Ser Pro Ala Lys Leu Ser Phe Gln Val Gly Phe Pro Ser
385                 390                 395                 400

Pro Val Leu Glu Met Phe Pro Ser Ser Gly Ser Ala Gln Val His Ile
                405                 410                 415

Pro Ser Ile Ser Val Asp Gly Leu Ser Thr Pro Val Val Leu Ser Pro
                420                 425                 430

Gly Pro Gln Lys Pro
                435

<210> SEQ ID NO 7
<211> LENGTH: 428
<212> TYPE: PRT
<213> ORGANISM: Homo sapiens

<400> SEQUENCE: 7

Met Asp Pro Ser Val Thr Leu Trp Gln Phe Leu Leu Gln Leu Leu Arg
1               5                   10                  15

Glu Gln Gly Asn Gly His Ile Ile Ser Trp Thr Ser Arg Asp Gly Gly
                20                  25                  30

Glu Phe Lys Leu Val Asp Ala Glu Val Ala Arg Leu Trp Gly Leu
        35                  40                  45

Arg Lys Asn Lys Thr Asn Met Asn Tyr Asp Lys Leu Ser Arg Ala Leu
50                  55                  60

Arg Tyr Tyr Tyr Asp Lys Asn Ile Ile Arg Lys Val Ser Gly Gln Lys
65                  70                  75                  80

Phe Val Tyr Lys Phe Val Ser Tyr Pro Glu Val Ala Gly Cys Ser Thr
                85                  90                  95

Glu Asp Cys Pro Pro Gln Pro Glu Val Ser Val Thr Ser Thr Met Pro
                100                 105                 110

Asn Val Ala Pro Ala Ala Ile His Ala Ala Pro Gly Asp Thr Val Ser
                115                 120                 125

Gly Lys Pro Gly Thr Pro Lys Gly Ala Gly Met Ala Gly Pro Gly Gly
                130                 135                 140

Leu Ala Arg Ser Ser Arg Asn Glu Tyr Met Arg Ser Gly Leu Tyr Ser
145                 150                 155                 160

Thr Phe Thr Ile Gln Ser Leu Gln Pro Gln Pro Pro Pro His Pro Arg
                165                 170                 175

Pro Ala Val Val Leu Pro Asn Ala Ala Pro Ala Gly Ala Ala Ala Pro
                180                 185                 190

Pro Ser Gly Ser Arg Ser Thr Ser Pro Ser Pro Leu Glu Ala Cys Leu
                195                 200                 205

Glu Ala Glu Glu Ala Gly Leu Pro Leu Gln Val Ile Leu Thr Pro Pro
210                 215                 220
```

-continued

```
Glu Ala Pro Asn Leu Lys Ser Glu Glu Leu Asn Val Glu Pro Gly Leu
225                 230                 235                 240

Gly Arg Ala Leu Pro Pro Glu Val Lys Val Glu Gly Pro Lys Glu Glu
            245                 250                 255

Leu Glu Val Ala Gly Glu Arg Gly Phe Val Pro Glu Thr Thr Lys Ala
        260                 265                 270

Glu Pro Glu Val Pro Pro Gln Glu Gly Val Pro Ala Arg Leu Pro Ala
    275                 280                 285

Val Val Met Asp Thr Ala Gly Gln Ala Gly Gly His Ala Ala Ser Ser
290                 295                 300

Pro Glu Ile Ser Gln Pro Gln Lys Gly Arg Lys Pro Arg Asp Leu Glu
305                 310                 315                 320

Leu Pro Leu Ser Pro Ser Leu Leu Gly Gly Pro Gly Pro Glu Arg Thr
                325                 330                 335

Pro Gly Ser Gly Ser Gly Ser Gly Leu Gln Ala Pro Gly Pro Ala Leu
            340                 345                 350

Thr Pro Ser Leu Leu Pro Thr His Thr Leu Thr Pro Val Leu Leu Thr
        355                 360                 365

Pro Ser Ser Leu Pro Pro Ser Ile His Phe Trp Ser Thr Leu Ser Pro
    370                 375                 380

Ile Ala Pro Arg Ser Pro Ala Lys Leu Ser Phe Gln Phe Pro Ser Ser
385                 390                 395                 400

Gly Ser Ala Gln Val His Ile Pro Ser Ile Ser Val Asp Gly Leu Ser
                405                 410                 415

Thr Pro Val Val Leu Ser Pro Gly Pro Gln Lys Pro
            420                 425

<210> SEQ ID NO 8
<211> LENGTH: 429
<212> TYPE: PRT
<213> ORGANISM: Mus musculus

<400> SEQUENCE: 8

Met Asp Pro Ser Val Thr Leu Trp Gln Phe Leu Leu Gln Leu Leu Arg
1               5                   10                  15

Glu Gln Gly Asn Gly His Ile Ile Ser Trp Thr Ser Arg Asp Gly Gly
                20                  25                  30

Glu Phe Lys Leu Val Asp Ala Glu Glu Val Ala Arg Leu Trp Gly Leu
            35                  40                  45

Arg Lys Asn Lys Thr Asn Met Asn Tyr Asp Lys Leu Ser Arg Ala Leu
50                  55                  60

Arg Tyr Tyr Tyr Asp Lys Asn Ile Ile Arg Lys Val Ser Gly Gln Lys
65                  70                  75                  80

Phe Val Tyr Lys Phe Val Ser Tyr Pro Glu Val Ala Gly Cys Ser Thr
                85                  90                  95

Glu Asp Cys Pro Pro Gln Pro Glu Val Ser Val Thr Ser Ala Ile Ala
            100                 105                 110

Met Ala Pro Ala Thr Ala His Ala Gly Pro Gly Asp Thr Ala Thr Gly
        115                 120                 125

Lys Pro Gly Thr Pro Lys Gly Ala Gly Met Thr Gly Gln Gly Gly Leu
    130                 135                 140

Ala Arg Ser Ser Arg Asn Glu Tyr Met Arg Ser Gly Leu Tyr Ser Thr
145                 150                 155                 160

Phe Thr Ile Gln Ser Leu Gln Pro Gln Pro Gln Pro Pro Ile Pro Pro
```

-continued

```
            165                 170                 175
Arg Pro Ala Ser Val Leu Pro Asn Thr Thr Pro Ala Gly Val Pro Ala
            180                 185                 190

Pro Ala Ser Gly Ser Arg Ser Thr Ser Pro Asn Pro Leu Glu Ala Cys
            195                 200                 205

Leu Glu Ala Glu Glu Ala Gly Leu Pro Leu Gln Val Ile Leu Thr Pro
            210                 215                 220

Pro Glu Ala Pro Asn Gln Lys Ser Glu Glu Leu Ser Leu Asp Pro Ser
225                 230                 235                 240

Phe Gly His Pro Gln Pro Pro Glu Val Lys Val Glu Gly Pro Lys Glu
                245                 250                 255

Glu Leu Glu Ala Ala Arg Ala Gly Gly Phe Ser Ser Glu Ala Val Lys
                260                 265                 270

Ala Glu Pro Glu Val Ser Ala Ser Glu Gly Leu Leu Ala Arg Leu Pro
                275                 280                 285

Ala Ile Leu Thr Glu Asn Thr Ala Gln Val Cys Gly Leu Ser Thr Ser
            290                 295                 300

Thr Thr Glu Ile Thr Gln Pro Gln Lys Gly Arg Lys Pro Arg Asp Leu
305                 310                 315                 320

Glu Leu Pro Leu Ser Pro Ser Leu Leu Gly Gly Gln Gly Pro Glu Arg
                325                 330                 335

Thr Pro Gly Ser Gly Thr Ser Ser Gly Leu Gln Ala Pro Gly Pro Ala
                340                 345                 350

Leu Thr Pro Ser Leu Leu Pro Thr His Thr Leu Thr Pro Val Leu Leu
                355                 360                 365

Thr Pro Ser Ser Leu Pro Pro Ser Ile His Phe Trp Ser Thr Leu Ser
            370                 375                 380

Pro Ile Ala Pro Arg Ser Pro Ala Lys Leu Ser Phe Gln Phe Pro Ser
385                 390                 395                 400

Ser Gly Ser Ala Gln Val His Ile Pro Ser Ile Ser Val Asp Gly Leu
                405                 410                 415

Ser Thr Pro Val Val Leu Ser Pro Gly Pro Gln Lys Pro
            420                 425
```

…

TRANSCRIPTION FACTORS IN NEURONAL DENDRITES-DENDRITIC PROTEIN SYNTHESIS AND CELL DEATH

CROSS-REFERENCE TO RELATED APPLICATIONS

This is a National Stage application of PCT International Application No. PCT/US2006/032513, filed Aug. 17, 2006, which in turn claims the benefit pursuant to 35 U.S.C. §119(e) of U.S. Provisional Application Nos. 60/708,981 and 60/736,993, filed on Aug. 17, 2005 and Nov. 15, 2005, respectively, each of which is hereby incorporated by reference in its entirety herein.

STATEMENT REGARDING FEDERALLY SPONSORED RESEARCH OR DEVELOPMENT

This invention was supported in part by funds obtained from the U.S. Government (National Institute of Mental Health grant numbers MH74169 and MH071705 and National Institutes of Health grant numbers AG9900 and MH58561), and the U.S. Government therefore has certain rights in the invention.

BACKGROUND OF THE INVENTION

A neuron is comprised of a nucleus within a body, or soma, a long fiber called the axon, and a varying number of branching fibers called dendrites, which extend out to other neurons. In recent years, a number of nuclear factors have been localized in the cytoplasm of neurons. Indeed, several nuclear transcription factors, such as Elk-1 (Sgambato et al., 1998, The Journal of Neuroscience 18: 214-226), ATF4 (Vernon et al., 2001, Molecular and Cellular Neuroscience 17: 637-645), NFκB (Lerner-Natoli et al., 2000, Epilepsy Research 41: 141-154) IκB (Yoshiyama et al., 2001, NeuroReport 12: 2641-2645) and CREB (Crino et al., 1998, Proc. Natl. Acad. Sci. USA 95: 2313-2318) have all been found in dendrites.

Elk-1 belongs to the ETS domain transcription factor family and the ternary complex factor (TCF) subfamily (Sharrocks et al., 2002, Biochemical Society Transactions 30:1-9). The deletion of Elk-1's DNA binding domain has been shown to eliminate Elk-1 DNA binding and subsequent Elk-1 transcriptional activity (Janknecht and Nordheim, 1992, Nuc. Acids Res. 20:3317-3324). In the nucleus, Elk-1 forms a ternary complex with the serum response factor (SRF) protein and the serum response element (SRE) promoter region. In addition to an N-terminal DNA binding domain, Elk-1 contains a "B box" mediating its interaction with SRF, a "C domain" acting as a transcriptional activation domain, two repression domains, and two domains which act as docking sites for multiple MAP kinases including ERK and JNK (Sharrocks et al., 2002, Biochemical Society Transactions 30:1-9). Activation of Elk-1 in the nucleus by phosphorylation is thought to impact neuronal differentiation (Sharrocks et al., 2001, Nature Reviews Molecular Cell Biology 2: 827-837), cell proliferation (Sharrocks et al., 2002, Biochemical Society Transactions 30:1-9), tumorigenesis (Chai et al., 2001, Oncogene 20: 1357-1367) and apoptosis (Sharrocks et al., 2002, Biochemical Society Transactions 30:1-9). Further, Elk-1 phosphorylation has been shown to be upregulated in response to the induction of both long-term depression (LTD) and long-term potentiation (LTP) in the hippocampus in vivo, suggesting a potential role for Elk-1 in synaptic plasticity (Thiels et al., 2002, The Journal of Neuroscience 22: 2054-2062; Davis et al., 2000, The Journal of Neuroscience 20: 4563-4572).

To date, the role or functional consequence of Elk-1 localization in dendrites has not been elucidated. An understanding of the role or function of a nuclear transcription factor localized in dendrites of a neuron would contribute to the understanding of regulation, metabolism and growth of neurons, and thus to more accurate and more useful control and manipulation of neurons. The development of such tools will enable precise, targeted therapies and treatments of all mammals, and in particular, of humans. Therefore, there exists a need for a better understanding of the function and role of Elk-1 in the cytoplasm of neurons in order to facilitate the controlled manipulation of cells. Further, there is a need in the art, satisfied by the present invention, to be able to modulate Elk-1 expression in a cell and thereby provide therapy to an individual having a neurodegenerative disease. The present invention addresses and meets these needs.

SUMMARY OF THE INVENTION

In one aspect, the invention features a method of altering competence of a dendrite, the method including the step of modulating the level of Elk-1 protein in a dendrite, thereby altering the competence of the dendrite. In one embodiment, the method includes increasing the level of Elk-1 protein by administering an activator of Elk-1 expression to the dendrite, wherein increasing the level of Elk-1 protein in a dendrite decreases competence of the dendrite. In one variation of this and other embodiments, administering an activator of Elk-1 expression includes introducing into the dendrite a heterologous translatable nucleic acid comprising an Elk-1 coding sequence, and expressing the heterologous translatable nucleic acid in the dendrite. In this and in other variations, the heterologous translatable nucleic acid is RNA. In another variation, the heterologous translatable nucleic acid contains an intron. In another variation, the RNA is provided to the dendrite by photoporation. In another another variation, decreasing the competence of a dendrite attached to a neuron leads to the death of the neuron. In yet another variation, decreasing competence of a dendrite leads to a decrease in the number of dendrites attached to a neuron.

In another embodiment of this aspect, the method includes decreasing the level of Elk-1 protein by administering an inhibitor of Elk-1 expression to the dendrite, wherein decreasing the level of Elk-1 protein in a dendrite increases competence of the dendrite. In this and other embodiments, the inhibitor is Elk-1 siRNA. In one variation, increasing the competence of a dendrite attached to a neuron leads to increased viability of the neuron.

In another aspect, the invention provides a method for altering viability of a neuron, the method including the step of modulating the level of Elk-1 protein in a neuron, thereby altering the viability of the neuron. In one embodiment, the method includes increasing the level of Elk-1 protein in a dendrite attached to the neuron by administering an activator of Elk-1 expression to the neuron. In another embodiment, the method includes decreasing the level of Elk-1 protein in a dendrite dendrite attached to the neuron by administering an inhibitor of Elk-1 expression to the neuron.

In another aspect, the invention provides a method of altering ATP level in a neuron, the method including the step of modulating the level of Elk-1 protein in a neuron, thereby altering the ATP level in the neuron. In one embodiment, the method includes increasing the level of Elk-1 protein in a dendrite attached to the neuron by administering an activator of Elk-1 expression to the dendrite, wherein increasing the level of Elk-1 protein in a dendrite decreases ATP level in the neuron. In one variation, decreasing ATP level in the neuron leads to increased susceptibility of the neuron to death. In another variation, the activator is administered to the neuron. In another embodiment, the method includes decreasing the level of Elk-1 protein in a dendrite attached to the neuron by administering an inhibitor of Elk-1 expression to the dendrite, wherein decreasing the level of Elk-1 protein in a dendrite increases the ATP level in the neuron. In one variation, the inhibitor is administered to the neuron.

In another aspect, the invention provides a method of at least one protein of a mitochondrial permeability transition pore complex, the method including the steps of contacting Elk-1 in a biological sample with an anti-Elk-1 antibody to produce an antigen/antibody complex, and isolating the antigen/antibody complex, thereby isolating at least one protein of a mitochondrial permeability transition pore complex. In one embodiment, the biological sample is selected from the group consisting of brain tissue, synaptoneurosomes and a mitochondrial fraction of fractionated neuronal tissue. In another embodiment, the at least one protein is selected from the group consisting of adenine nucleotide transporter (ANT), voltage-dependent anion channel (VDAC), ubiquitous mitochondrial creatine kinase (uMTCK) and hexokinase (HXK). In another aspect, the invention provides a kit for isolating a a mitochondrial permeability transition pore complex protein, the kit including a sample container for carrying a biological sample, an antibody directed against Elk-1 protein, a positive control solution comprising isolated Elk-1 protein and at least one isolated mitochondrial permeability transition pore complex protein, and an instructional material.

In another aspect, the invention provides a composition including isolated Elk-1 protein and at least one isolated mitochondrial permeability transition pore complex protein. In one embodiment, the mitochondrial permeability transition pore complex protein is selected from the group consisting of adenine nucleotide transporter (ANT), voltage-dependent anion channel (VDAC), ubiquitous mitochondrial creatine kinase (uMTCK) and hexokinase (HXK).

The invention, in another aspect, provides a method of introducing an RNA into a neuron, the method including contacting a neuron with an RNA, and photoporating the neuron at one or more sites, thereby introducing the RNA into the neuron. In one embodiment, the photoporating step includes photoporating one or more sites on one or more dendrites of the neuron. IN another aspect, the invention provides a method of translating an RNA in a dendrite, the method including the steps of contacting a neuron with a translatable RNA, photoporating the neuron at one or more sites on one or more dendrites attached to the neuron, and allowing translation of the translatable RNA to occur, thereby translating the RNA in the dendrite. In one embodiment, the translatable RNA includes at least one intron.

The invention, in yet another aspect, provides a method for treating a neurodegenerative disease in an individual, the method including the steps of decreasing the level of Elk-1 protein in a dendrite attached to a neuron in an individual diagnosed with a neurodegenerative disease by administering an inhibitor of Elk-1 expression, wherein decreasing the level of Elk-1 protein in the dendrite increases viability of the neuron, thereby treating the neurodegenerative disease. In one embodiment, the neurodegenerative disease is selected from the group consisting of Huntington's disease, Alzheimer's disease and Parkinson's disease.

In another aspect, the invention provides a method of alleviating a neurodegenerative disease in an individual, the method including the steps of administering a neuroprotectant to a neuron in an individual diagnosed with a neurodegenerative disease, wherein the neuroprotectant is an attenuator of Elk-1 protein specific activity, thereby increasing viability of the neuron and alleviating the neurodegenerative disease. In one embodiment, the neuroprotectant increases SUMOylation of Elk-1 protein in the dendrite. In another embodiment, the neuroprotectant decreases phosphorylation of Elk-1 protein in the dendrite. In a variation of this and other embodiments, the neuroprotectant is a MEK/ERK cascade inhibitor. In this and in other variations, the MEK-ERK cascade inhibitor is selected from the group consisting of SL327, PD98059, U0126 and 5-iodotubercidin.

In yet another aspect, the invention provides a method for monitoring risk of degeneration in a neuron, the method including the steps of detecting a first level of Elk-1 protein in a dendrite of a neuron, and detecting a second level of Elk-1 protein in a dendrite of the neuron, wherein the second level is detected at a time after the first level is detected, and wherein an increase in the second level compared to the first level is indicative of increased risk of degeneration of the neuron.

In another aspect, the invention provides a method of altering competence of a dendrite, the method including the step of altering the specific activity of Elk-1 protein in a dendrite, thereby altering the competence of the dendrite. In one embodiment, the method includes increasing the specific activity of Elk-1 protein in a dendrite by administering an amplifier of Elk-1 specific activity to the dendrite, wherein increasing the specific activity of Elk-1 protein in a dendrite decreases competence of the dendrite. In one variation of this and other embodiments, administering an amplifier of Elk-1 specific activity includes administering a compound to the dendrite, wherein the compound decreases SUMOylation of Elk-1 protein in the dendrite. In another variation of this and other embodiments, administering an amplifier of Elk-1 specific activity includes administering a compound to the dendrite, wherein the compound increases phosphorylation of Elk-1 protein in the dendrite. In another variation, decreasing competence of a dendrite attached to a neuron leads to death of the neuron. In another variation, decreasing competence of a dendrite attached to a neuron leads to a decrease in the number of dendrites attached to the neuron.

In another embodiment of this aspect, the method includes decreasing the specific activity of Elk-1 protein in a dendrite by administering an attenuator of Elk-1 specific activity to the dendrite, wherein decreasing the specific activity of Elk-1 protein in a dendrite increases competence of the dendrite. In one variation of this and other embodiments, administering an attenuator of Elk-1 specific activity includes administering a compound to the dendrite wherein the compound increases SUMOylation of Elk-1 protein in the dendrite. In another variation of this and other embodiments, administering a compound to the dendrite, wherein the compound decreases phosphorylation of Elk-1 protein in the dendrite. In a variation of this and other embodiments, the compound is a MEK/ERK cascade inhibitor. In this and in other variations, the MEK-ERK cascade inhibitor is selected from the group consisting of SL327, PD98059, U0126 and 5-iodotubercidin. In another variation, increasing the competence of a dendrite attached to a neuron leads to increased viability of the neuron.

In another aspect of the invention, a method is provided of altering the viability of a neuron, the method including the step of altering the specific activity of Elk-1 protein in a dendrite attached to a neuron, thereby altering viability of the neuron. In one embodiment, the method includes the step of increasing the specific activity of Elk-1 protein in the dendrite by administering an amplifier of Elk-1 specific activity to the neuron, wherein increasing the specific activity of Elk-1 protein in the dendrite decreases viability of the neuron. In one variation, decreasing viability of a neuron leads to a decrease in the number of dendrites attached to the neuron. In another embodiment, the method includes the step of decreasing the specific activity of Elk-1 protein in the dendrite by administering an attenuator of Elk-1 specific activity to the neuron, wherein decreasing the specific activity of Elk-1 protein in the dendrite increases viability of the neuron.

In another aspect, the invention provides a method of altering ATP level in a neuron, the method including the step of altering the specific activity of Elk-1 protein in a dendrite attached to a neuron, altering the specific activity of Elk-1 protein in a dendrite attached to a neuron. In one embodiment, the method includes increasing the specific activity of Elk-1 protein in a dendrite by administering an amplifier of Elk-1 specific activity to the dendrite, wherein increasing the specific activity of Elk-1 protein in the dendrite decreases ATP level in the neuron. In one variation, decreasing ATP level in the neuron leads to increased susceptibility of the neuron to death. In another variation, the activator is administered to the neuron. In another embodiment, the method includes decreasing the specific activity of Elk-1 protein in a dendrite by administering an attenuator of Elk-1 specific activity to the dendrite, wherein decreasing the specific activity of Elk-1 protein in the dendrite increases ATP level in the neuron. In another variation, the attenuator is administered to the neuron.

In yet another aspect, the invention provides a method for treating a neurodegenerative disease in an individual, the method including the step of decreasing the specific activity of Elk-1 protein in a dendrite attached to a neuron in an individual diagnosed with a neurodegenerative disease by administering an attenuator of Elk-1 specific activity, wherein decreasing the specific activity of Elk-1 protein in the dendrite increases viability of the neuron, thereby treating the neurodegenerative disease. In one embodiment, the neurodegenerative disease is selected from the group consisting of Huntington's disease, Alzheimer's disease and Parkinson's disease.

In yet another aspect, the invention provides a method for treating a neurodegenerative disease in an individual, the method including the step of decreasing the specific activity of Elk-1 protein in a dendrite attached to a neuron in an individual diagnosed with a neurodegenerative disease by administering an inhibitor of mitochondrial PTP opening or an inhibitor of Elk-1 transcriptional activity, wherein decreasing the specific activity of Elk-1 protein in the dendrite increases viability of the neuron, thereby treating the neurodegenerative disease. In one embodiment, the neurodegenerative disease is selected from the group consisting of Huntington's disease, Alzheimer's disease and Parkinson's disease.

A method of identifying a compound useful for the treatment of a neurodegenerative disease, the method including the steps of increasing the level of Elk-1 protein in a dendrite attached to a first neuron; contacting the dendrite with a test compound; assessing the viability of the first neuron; and assessing the viability of a second, otherwise identical neuron that is not contacted with the test compound; wherein a test compound that increases the viability of the first neuron compared to the second neuron is a compound useful for the treatment of a neurodegenerative disease. In one embodiment, the test compound is selected from the group consisting of a mitochondrial PTP inhibitor, a suspected mitochondrial PTP inhibitor, an Elk-1 transcriptional inhibitor and a suspected Elk-1 transcriptional inhibitor.

In another aspect, the invention provides a method for monitoring risk of degeneration in a neuron, the method including the steps of detecting a first specific activity of Elk-1 protein in a dendrite of a neuron, and detecting a second specific activity of Elk-1 protein in a dendrite of the neuron, wherein the second specific activity is detected at a time after the first specific activity is detected, and wherein an increase in the second specific activity compared to the first specific activity is indicative of increased risk of degeneration of the neuron.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1 is a series of immunofluorescent images of primary rat hippocampal neurons.

FIG. 2 is a series of images depicting Elk-1 RNA localization and translation in dendrites.

FIG. 3A is a table summarizing mitochondrial proteins of the permeability transition pore (PTP) that co-immunoprecipitate with Elk-1. Co-immunoprecipitations were from mouse whole brain (WB), synaptoneurosome (SN) and mitochondrial (MT) fractions. Check marks indicate the antibody and tissue conditions that led to the identification of the mitochondrial proteins.

FIG. 7 is a series of images depicting dendrite degeneration and cell death resulting from locally translated Elk-1 protein.

FIG. 8 is a series of graphs and images regarding Elk-1 mediated cell death, Elk-1 transcription and activity of the mitochondrial PTP. In the images, lightning bolts represent regions of photoporation. Dotted circles show area where one would expect to see nuclear dye accumulation in the photoporated neurons of cells were dead.

GFP mRNA following pre-incubation with the transcriptional inhibitor actinomycin D). Images on the right-hand side were taken approximately 4 hours after photoporation to assess cell death. Small images in inset are of GFP fluorescence through the XY, YZ and XZ planes in a neuron after photoporation of Elk-1 GFP mRNA into a distal dendrite.

FIG. 9, consisting of FIGS. 9A, 9B and 9C, depicts representative images of stained human tissue obtained from a patient diagnosed with Parkinson's disease.

FIG. 10, comprising FIG. 10A depicts tangle-containing neurons. FIG. 10B depicts diffuse plaques regions. FIG. 10B is at 10× magnification.

FIG. 11, comprising FIG. 11A depicts neurons with protein aggregates that also contain concentrated Elk-1 staining (indicated by arrows). FIG. 1B depicts an neuron with concentrated Elk-1 staining that contains a large inclusion body.

DETAILED DESCRIPTION OF THE INVENTION

Figures 1A, 1B, 1C:
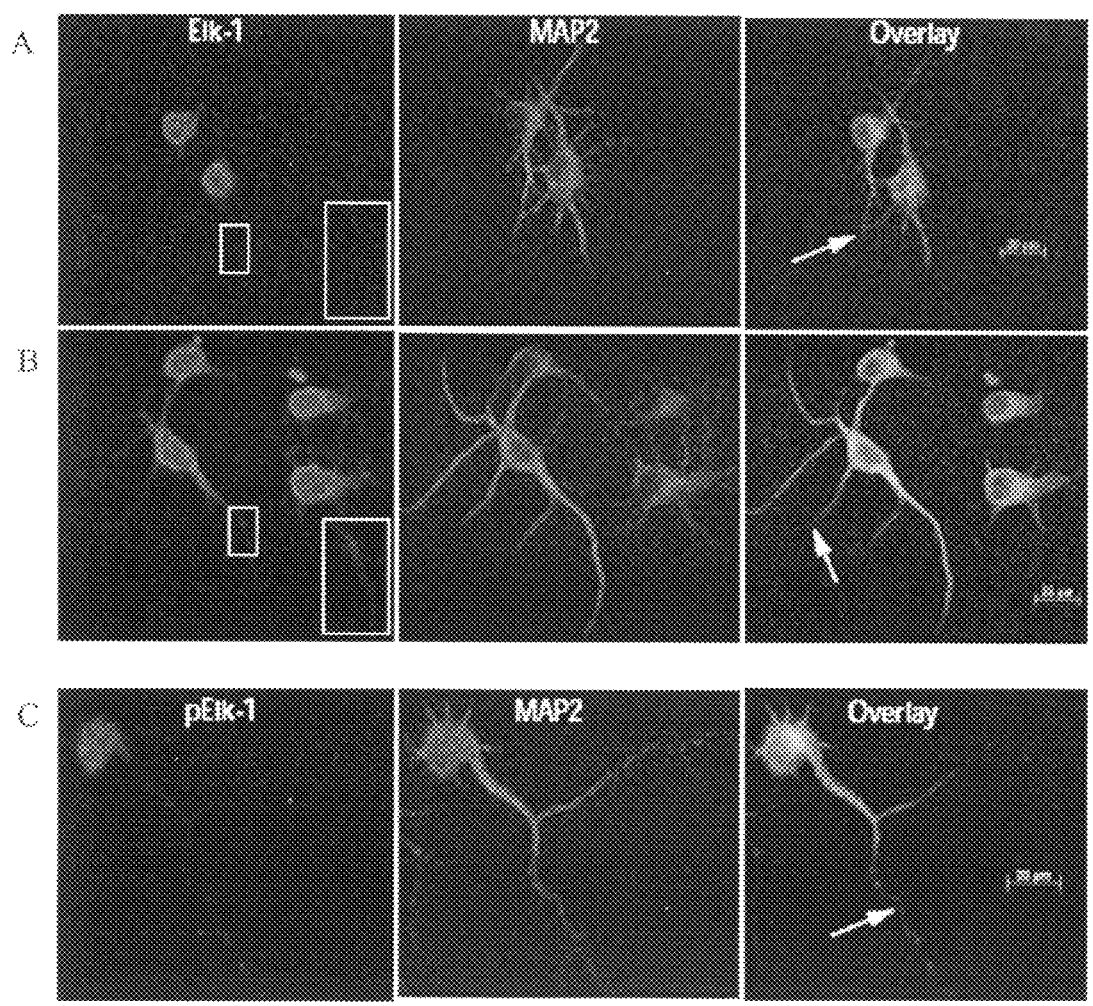
FIG. 1A depicts Elk-1 immunoreactivity in proximal and distal dendrites. Inset shows a magnified image of an individual dendrite.
FIG. 1B depicts Elk-1 immunoreactivity after a 30-minute application of DHPG (50 μM; n=7). Inset shows a magnified image of an individual dendrite.
FIG. 1C depicts phospho-Elk-1 immunoreactivity in proximal and distal dendrites. Elk-1 was detected using Cy3. MAP2 was detected using Alexa 488. Merged images show immunodetection of Elk-1 and MAP2 (FIGS. 1A and 1B) or phospho-Elk-1 and MAP2 (FIG. 1C). Arrows highlight regions of Elk-1 immunoreactivity in dendrites. Scale bar=20 μm.

Several nuclear factors have been localized in the cytoplasm of neurons. Some nuclear factors, including the nuclear transcription factor Elk-1, have been detected in dendrites. Determining the role of dendritically-localized nuclear transcription factors in the cellular function of neurons is important for understanding normal neuronal function and neurodegenerative diseases. The present invention addresses this need. Specifically, the present invention springs from the unexpected observation that dendritically localized Elk-1 influences neuronal viability and ATP levels, and can effect dendritic degeneration and neuronal cell death. The present invention thus provides methods of altering dendritic competence or neuronal viability, and other methods related thereto.

The present invention further provides a novel method for controlled and localized introduction of nucleic acid into neurons.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

Standard techniques are used for nucleic acid and peptide synthesis. The techniques and procedures are generally performed according to conventional methods in the art and various general references (e.g., Sambrook and Russell, 2001, Molecular Cloning, A Laboratory Approach, Cold Spring Harbor Laboratory Press, Cold Spring Harbor, N.Y., and Ausubel et al., 2002, Current Protocols in Molecular Biology, John Wiley & Sons, New York, N.Y.), which are provided throughout this document.

The articles "a" and "an" are used herein to refer to one or to more than one (i.e., to at least one) of the grammatical object of the article. By way of example, "an element" means one element or more than one element.

The term "modulating the level of Elk-1 protein" as used herein refers to either increasing or decreasing the level of Elk-1 protein compared to the level of Elk-1 protein in the absence of the modulation.

The term "coding sequence" as used herein refers to the nucleotide sequence that directly specifies the amino acid sequence of the encoded protein product. A coding sequence as used herein can include introns, as well as nucleotide sequences corresponding to amino acid residues, which are not present in the mature protein encoded by coding sequence (e.g., amino acid residues in a protein export signal sequence).

A "translatable nucleic acid" as used herein refers to a nucleotide sequence containing a coding sequence operably fused to nucleotide sequences necessary for translation. Such sequences include, but are not limited to, ribosome binding sites and Kozak sequences.

As used herein, a "heterologous translatable nucleic acid" refers to a translatable nucleic acid that is not endogenous to a cell. It encompasses translatable RNA nucleic acids and translatable nucleic acids contained in an expression vector. It further encompasses mRNA isolated from a neuron and that is introduced back into a neuron from the same organism.

As used herein, amino acids are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |

| Full Name | Three-Letter Code | One-Letter Code |
|---|---|---|
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand" or "sense strand"; sequences on the DNA strand which are located 5' to a reference point on the DNA are referred to as "upstream sequences"; sequences on the DNA strand which are 3' to a reference point on the DNA are referred to as "downstream sequences."

A "portion" of a polynucleotide means at least at least about twenty sequential nucleotide residues of the polynucleotide. It is understood that a portion of a polynucleotide may include every nucleotide residue of the polynucleotide.

As used herein "siRNA" refers to small interfering RNAs, which are involved in the phenomenon of RNA interference (RNAi). siRNAs are typically about 21 to about 25 nucleotides long, are double-stranded and 100% homologous to a portion of a coding sequence. However, as used herein, the term "siRNA" encompasses all forms of siRNA including, but not limited to (i) a double stranded RNA polynucleotide, (ii) a single stranded polynucleotide, and (iii) a polynucleotide of either (i) or (ii) wherein such a polynucleotide, has one, two, three, four or more nucleotide alterations or substitutions therein. If an siRNA is single stranded, its sequence is homologous to a portion of the antisense strand of a coding sequence.

"Elk-1 siRNA" as used herein refers to an RNA molecule which is homologous to a portion of an Elk-1 coding sequence, or if single stranded, a portion of the antisense strand of an Elk-1 coding sequence. Preferably, the siRNA is 100% homologous to a portion of an Elk-1 coding sequence or antisense strand.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

As used herein, "recombinant polynucleotide" refers to a polynucleotide having sequences that are not naturally joined together. An amplified or assembled recombinant polynucleotide may be included in a suitable vector, and the vector can be used to transform or transfect a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide." As used herein, a host cell is a neuronal cell.

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

As used herein, an "isolated protein" refers to a protein that is substantially free of other cellular material, or culture medium when produced by recombinant techniques, or substantially free of chemical precursors or other chemicals when chemically synthesized. A mitochondrial PTP protein that is substantially free of cellular material includes preparations of a mitochondrial PTP protein having less than about 30%, 20%, 10%, or 5% (by dry weight) of non-mitochondrial PTP protein, excluding Elk-1 protein.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, intracellular antibodies ("intrabodies"), Fv, Fab and F(ab)$_2$, as well as single chain antibodies (scFv) and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426). As used herein, a "neutralizing antibody" is an immunoglobulin molecule that binds to and blocks the biological activity of the antigen.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, to "alleviate" a disease, disorder or condition means reducing the severity of one or more symptoms of the disease, disorder or condition.

As used herein, to "treat" means reducing the frequency with which symptoms of a disease, disorder, or adverse condition, and the like, are experienced by a patient.

As used herein, the term "remodel" relates to an alteration of the state or condition of something from a previous state or condition. For example, a neural network is "remodeled" as a result of a procedure or treatment if at least one neural connection or interface is changed from a previous state or condition as a result of the procedure or treatment.

The term "dendrite contact," as used herein, indicates physical contact of a dendrite with another physiological structure, including, but not limited to a second dendrite, an axon, a neurite, or a soma.

The term "dendrite interaction" or "interaction with a dendrite" indicates at least one of chemical and physical contact of a dendrite with another physiological structure, but does not require physical contact with a dendrite.

As used herein, "dendrite competence" refers to the number and extent of morphological features of a dendrite, including, but not limited to dendritic spines, dendritic branching, synapses and other dendritic specializations. "Dendrite competence" is used interchangeably with "competence of a dendrite". An increase in dendrite competence is indicated by an increase in number or extent of at least one of dendritic spines, dendritic branching, synapses and other dendritic specializations. Similarly, a diminution in dendrite competence is indicated by a decrease in number or extent of at least one of dendritic spines, dendritic branching, synapses and other dendritic specializations. As used herein, "dendritic degeneration" is synonomous with a diminution in dendrite competence.

As used herein, "dendritically localized Elk-1" refers to Elk-1 protein in a dendrite. The source of the Elk-1 protein in the dendrite may be either endogenous (e.g., expression of an endogenous Elk-1 gene) or exogenous (any source other than expression of an endogenous Elk-1 gene). Dendritically localized Elk-1 may be different from Elk-1 localized elsewhere in a neuron, e.g., the cell body, by way of post-translational modification, including, but not limited to, phosphorylation, SUMOylation, glycosylation, sulfation, acetylation, and alkylation.

As used herein, "specific activity of Elk-1 protein" refers to the capacity of dendritically localized Elk-1 protein to induce, either directly or indirectly, at least one of a diminution in dendrite competence or neuronal cell death. An increased specific activity therefore is an increased capacity to induce at least one of a diminution in dendritic competence or neuronal cell death, compared to the basal specific activity of dendritically localized Elk-1. Similarly, a decreased specific activity is a decreased capacity to induce at least one of a diminution of dendritic degeneration or neuronal cell death, compared to the basal specific activity of dendritically localized Elk-1.

As used herein, "neuronal viability" refers generally to the health of a neuron or collection of neurons. In a collection of neurons, the number of living neurons may be a measure of neuronal viability. In a neuronal culture, neuronal viability may also be assessed by the duration of neuronal survival. In an individual neuron, neuronal viability may be assessed, for instance, by metabolic measures or by morphological features. Such morphological features include, but are not limited to, cytoplasmic swelling, the number of dendrites attached to the neuron, the number of synapses associated with the neuron, the extent of dendrite branching, the extent of dendritic specializations, and membrane integrity. As used herein, "neuronal degeneration" is synonomous with decreased neuronal viability. Indications of decreased neuronal viability include, but are not limited to, an increase in cytoplasmic swelling, a decrease in the number of dendrites attached to the neuron, a decrease in the number of synapses associated with the neuron, a decrease in the branching of the dendrites or in dendritic specializations, such as spines, and a decrease in nucleus integrity.

As used herein, "otherwise identical neuron" refers to a neuron from the same species of organism and same type of neuronal tissue that another neuron is from, and subjected to the same conditions, such as culture conditions, as the other neuron. Preferably, the otherwise identical neuron comes from the same neuronal tissue source as the other neuron.

As used herein, the term "synaptic network" refers to an interconnected network of neurons, and may include other components.

The term "neural network" also refers to a network of neurons, and may include other components.

As used herein, a "neuroprotectant" is a compound that increases or prolongs neuronal viability, thereby inhibiting or delaying neuronal degeneration and cell death. The compound may be any type of molecule, including but not limited to small molecules, peptides, polypeptides, proteins, DNA, RNA, peptidomimetics, and peptide nucleic acids.

Description of The Invention

In the present invention, it is demonstrated for the first time that a locally synthesized protein is capable of modulating neuronal cell viability. Specifically, dendritically synthesized Elk-1 can produce dendritic degeneration and subsequent neuronal cell death. It is shown for the first time herein that increasing the level of Elk-1 protein or the specific activity of Elk-1 protein in a dendrite, or in a whole neuron, decreases the dendrite competence and/or viability of the cell. It is further shown that these effects require Elk-1 transcriptional activity. It is further shown for the first time herein that the number of dendrites per neuron also decreases when the level of Elk-1 protein or the specific activity of dendritically localized Elk-1 protein is increased. It is also shown for the first time herein that increasing the level of Elk-1 protein or the specific activity of Elk-1 protein in a dendrite, or in the whole neuron, causes a decrease in ATP levels in the neuron. Decreasing the level or specific activity of Elk-1 protein in a dendrite, or in the whole neuron, increases cell viability and increases ATP levels, as is shown for the first time herein. Furthermore, the association of dendritically localized Elk-1 with mitochondrial permeability transition pore (PTP) complexes is demonstrated herein for the first time. Specifically, Elk-1 association with adenine nucleotide transporter (ANT), voltage-dependent anion channel (VDAC), ubiquitous mitochondrial creatine kinase (uMTCK) and hexokinase (HXK) is shown herein. It is further shown herein that Elk-1 mediated cell death requires mitochondrial PTP function. It is further shown herein that Elk-1 transcriptional activity is necessary for Elk-1 mediated cell death. Furthermore, a technique for introducing RNA locally into a live, intact dendrite, permitting increased control over local RNA expression and resultant protein levels, is demonstrated herein.

Therefore, the present application features methods of altering the competence of a dendrite or the viability of a neuron. This is because modulating the level or specific activity of Elk-1 in a dendrite alters the competence of the dendrite and the viability of the neuron that has the dendrite. Accordingly, the present invention also features methods of treating a neurodegenerative disease in an individual and methods of alleviating a neurodegenerative disease in an individual. The invention also features methods of altering the ATP levels in a neuron. The invention further features a method of assessing risk of neurodegeneration of a neuron.

The present invention also features methods of isolating at least one protein of a mitochondrial permeability transition pore complex. This is because dendritically localized Elk-1 is associated with mitochondrial permeability transition pore complexes.

The invention further provides methods of introducing an RNA into a neuron. Further, the invention provides methods of translating an RNA in a dendrite.

The methods of the instant invention can be practiced using any neuron or dendrite of a neuron. Preferred neurons are those of mammals, including both non-human mammals as well as humans. Particularly preferred neurons in the practice of the instant invention are those of rats, mice and humans. The methods of the instant invention may be practiced using a dendrite that is isolated, or using a dendrite that is a component of a neuron. That is, in the latter instance, the dendrite is attached to a neuron comprising at least a soma. The methods of the invention may also be practiced using an isolated neuron, or a neuron in a neural network. An isolated neuron can be maintained in culture, including primary cell culture and slice culture. Furthermore, the methods of the invention may be practiced using a neuron that is in vivo, in a living organism. The neuron can also be a transplanted neuron, either in vitro in culture or in vivo in an animal. The neuron may also be a transplanted neuron that is not a part of a neural network, but has the potential to be stimulated to integrate into an existing neural network.

The methods of the instant invention have myriad useful applications. In general, the methods and compositions of the present invention are useful in neurobiological research including neurodegenerative disease research, drug development for neurodegenerative diseases and therapeutic methods for neurodegenerative diseases. The method of decreasing dendrite competence or neuronal viability can, for instance, be used in analyzing the effect on a neural network of the death of a single neuron in a neural network. The method of decreasing dendrite competence or neuronal viability also has therapeutic applications to alleviate or treat disorders, diseases or conditions characterized by undesirable or excess neuronal contacts. The method of increasing dendrite competence or neuron cell viability is useful, for instance, in prolonging viability of neurons in culture, or for increasing viability of a transplanted neuron. The method of increasing dendrite competence or neuronal cell viability also has therapeutic applications to alleviate or treat disorders, diseases or conditions characterized by neuronal cell death or accelerated neuronal death. Neurodegenerative disorders, diseases and conditions for which the methods of the invention may be useful include, but are not limited to, Parkinson's disease, Alzheimer's disease, Huntington's disease, amyotrophic lateral sclerosis, Fragile X syndrome, Downs' syndrome, and neuropsychiatric illnesses, such as depression, schizophrenia, and schizo-affective disorders. Notably, it is demonstrated herein that an over-abundance of Elk-1 protein is associated with the presence of pathological markers of Parkinson's disease, Alzheimer's disease and Huntington's disease.

The methods of introducing an RNA locally into a dendrite, and translating an RNA so introduced are useful, for instance, in studying the effect on a dendrite or neuron of dendritically localized translation of a coding sequence of interest. These methods find application in studying synaptic plasticity at a single dendrite level. These methods are also useful in providing dendritically localized RNAs in neurons that are subsequently transplanted. The RNAs in this use may encode proteins that alter synaptic plasticity to improve transplantation outcome, including increasing the viability or ATP level of the neuron.

The method of isolating at least one protein of a mitochondrial PTP is useful as a rapid means for isolating such proteins, and provides a composition comprising isolated Elk-1 protein and at least one mitochondrial PTP protein. The composition is useful in screening for inhibitors of the association of Elk-1 and at least one protein of a mitochondrial PTP, in order to develop therapeutics and diagnostics for neurodegenerative diseases.

The method for assessing risk of degeneration of a neuron is useful for enabling early intervention to prevent or delay the predicted neurodegeneration. It is also useful for monitoring neuronal viability in cultures.

Modulating Levels of Elk-1 Protein

The instant invention includes methods of altering the competence of a dendrite and/or the viability of a neuron by modulating the level of Elk-1 protein in a dendrite or neuron. As shown in the examples presented herein, increasing the level of Elk-1 protein in a dendrite and/or neuron decreases the competence of the dendrite and/or the viability of the neuron. Decreasing competence of a dendrite may or may not lead to the decreased viability or death of the neuron to which the dendrite is attached.

In one embodiment, the method of altering dendrite competence or neuron viability includes increasing the level of Elk-1 protein in a dendrite or neuron by administering an activator of Elk-1 expression, thereby decreasing competence of the dendrite and/or viability of the neuron. As used herein, an "activator of Elk-1 expression" is any compound that increases the level of Elk-1 protein, preferably dendritically localized Elk-1 protein. An activator may directly or indirectly increase Elk-1 expression.

Increasing the level of Elk-1 protein can be accomplished using methods known to the skilled artisan. Such methods include, but are not limited to, providing exogenous Elk-1 protein to a dendrite, expressing a recombinant Elk-1 gene, upregulating expression of an endogenous Elk-1 gene, increasing the half-life or stability of Elk-1 mRNA localized in dendrites, increasing the expression of dendritically localized Elk-1 mRNA, and/or decreasing the local concentration of dendritically localized Elk-1 protein. An activator of Elk-1 expression, therefore, may be a nucleic acid encoding Elk-1, a compound that upregulates Elk-1 expression or upregulates expression of Elk-1 gene-specific transcriptional activator proteins, a compound that increases the transport of Elk-1 mRNA from the nucleus to the dendrites, a compound that increases the amount, half-life or stability of Elk-1 mRNA, or a compound that decreases the degradation of dendritically localized Elk-1 protein.

In a preferred embodiment, increasing expression of dendritically localized Elk-1 mRNA is used to effect an increase in the level of Elk-1 protein in the dendrite. This is accomplished by administering an mGluR agonist to a neuron, thereby increasing translation of Elk-1 mRNA. Non-limiting examples of an mGluR agonist include dihydrophenylglycine (DHPG), (1S,3R)-1-aminocyclopentane-1,3-dicarboxylic acid (ACPD) and quisqualate.

In another preferred embodiment, increasing the expression of dendritically localized Elk-1 mRNA is accomplished by introducing heterologous translatable RNA encoding Elk-1 into a dendrite. As will be understood by the skilled artisan, translatable RNA useful in the present invention is prepared in any number of ways, and the method of preparation of RNA should not be considered to limit the invention in any way. By way of a non-limiting example, RNA useful in the present invention may be prepared by methods including isolation of native Elk-1 mRNA, including pre-mRNA, from a cell, isolation of Elk-1 encoding RNA from a recombinant system in which a recombinant DNA construct was used to transcribe RNA, or from a recombinant RNA virus (e.g., rhinovirus, hepatitis C), modified to contain a translatable Elk-1 coding sequence. The RNA encoding Elk-1 is introduced into a dendrite, preferably using photoporation as described below.

In one embodiment of the invention, the translatable RNA contains at least one intron. An RNA splicing donor/acceptor pair for the at least one intron can be a canonical pair, an atypical pair or a cryptic pair.

In another aspect, heterologous translatable RNA encoding Elk-1 is introduced into a dendrite or neuron using methods known in the art. One method is lipid-mediated introduction of RNA into a dendrite. Preferably, RNA is introduced using photoporation. The translatable RNA can be introduced at one or more sites on one or more dendrites. The dendrite can either be a proximal dendrite or a distal dendrite with respect to the body of the neuron. When two or more dendrites are sites for photoporation, the dendrites may be all distal dendrites, all proximal dendrites, or both distal and proximal dendrites.

In another embodiment, the level of Elk-1 protein in a dendrite is increased by expression of a heterologous translatable nucleic acid encoding Elk-1 contained in an expression vector. As will be understood by the skilled artisan, introducing an expression vector into a neuron can be accomplished in any number of ways, and the method of introducing an expression vector should not be considered as limiting the invention in any way. Expression vectors and methods for the introduction of exogenous DNA into cells with concomitant expression of the exogenous DNA in the cells are described, for example, in Sambrook et al. (2001, Molecular Cloning: A Laboratory Manual, Cold Spring Harbor Laboratory Press, Cold Spring Harbor, N.Y.), and in Ausubel et al. (eds, 1997, Current Protocols in Molecular Biology, John Wiley & Sons, New York, N.Y.). Any expression vector compatible with the expression of proteins in neurons is suitable for use in the instant invention, and can be selected from the group consisting of a plasmid DNA, a viral vector, and a mammalian vector. The expression vector, or a vector that is co-introduced with the expression vector, can further comprise a marker gene. Marker genes are useful, for instance, to monitor transfection efficiencies. Marker genes include: genes for selectable markers, including but not limited to, G418, hygromycin, and methotrexate, and genes for detectable markers, including, but not limited to, luciferase and GFP. The expression vector can further comprise an integration signal sequence which facilitates integration of the isolated polynucleotide into the genome of a neuronal cell.

The Elk-1 coding sequence contained in either translatable RNA or an expression vector may, optionally, be fused in-frame to other coding sequences. For instance, the coding sequence of an epitope or other detectable tag may be included. Such tags are useful, for instance, to monitor expression of the recombinant polypolypeptide in a transfected neuron. Other useful coding sequences are those allowing for rapid purification of the encoded Elk-1, such as 6-His. The fusion may be at either the N-terminal or the C-terminal of Elk-1.

Numerous Elk-1 genes have been cloned and sequenced, and any one can be used in the instant invention. Elk-1 coding sequences useful in the instant invention include, but are not limited to: rat Elk-1 (Accession number XM_001078496; SEQ ID NO. 1, nucleotide; SEQ ID NO. 6, amino acid), human Elk-1 (Accession number NM_005229; SEQ ID NO. 2, nucleotide; SEQ ID NO. 7, amino acid), and mouse Elk-1 (Accession number BC054474; SEQ ID NO. 3, nucleotide; SEQ ID No. 8, amino acid). Furthermore, any sequence encoding a variant Elk-1 protein can be used, provided the Elk-1 variant protein has the function of decreasing dendrite or neuron viability when over-expressed in a dendrite or neuron, and can associate with mitochondrial PTP, as shown herein. Methods for assessing these functions are discussed herein where preferred methods are set forth in the examples herein. In a preferred embodiment, the Elk-1 coding sequence, or variant thereof, is from the same organism as is the neuron.

In another embodiment, the method of decreasing dendrite competence or neuron viability includes increasing the level of Elk-1 protein in a dendrite or neuron by providing exogenous Elk-1 protein. The exogenous Elk-1 protein may be identical in sequence to the endogenous Elk-1 protein or may be a different sequence. The exogenous protein may also be a hybrid or fusion protein to facilitate distinguishing it from endogenous Elk-1 or to faciliatate its entry in the targeted dendrite or neuron. For instance, a hybrid Elk-1 protein may comprise a receptor targeting sequence. The skilled artisan is familiar with methods of delivering protein to a cell, including, but not limited to, photoporation, liposomes and other lipid formulations. Any method of delivering a protein to a dendrite or neuron is suitable in the practice of the invention.

As is also demonstrated in the examples included herein, decreasing the level of Elk-1 protein in a dendrite or neuron, increases dendrite competence and/or the viability of the neuron. Therefore, in another embodiment, the method of altering the competence of a dendrite or viability of a neuron neuron includes decreasing the level of Elk-1 protein in a dendrite or neuron by administering an inhibitor of Elk-1 expression to the dendrite or neuron, thereby increasing the dendrite competence and/or viability of the neuron. As used herein, an "inhibitor of Elk-1 expression" is any compound that decreases the level of Elk-1 protein, preferably dendritically localized Elk-1 protein. An inhibitor may directly or indirectly decrease Elk-1 expression.

Decreasing the level of Elk-1 protein can be accomplished using any method known to the skilled artisan. Examples of methods to decrease the level of Elk-1 protein include, but are not limited to decreasing expression of an endogenous Elk-1 gene, decreasing expression of Elk-1 mRNA, and increasing local concentration of dendritically localized Elk-1 protein. An inhibitor of Elk-1 expression may therefore be a compound that decreases expression of an Elk-1 gene, a compound that decreases Elk-1 mRNA half-life, stability and/or expression, or a compound that increases degradation of dendritically localized Elk-1 protein.

Decreasing expression of an endogenous Elk-1 gene includes providing a specific inhibitor of Elk-1 gene expression. Decreasing expression of Elk-1 mRNA includes decreasing the half-life or stability of dendritically localized Elk-1 mRNA or decreasing expression of Elk-1 mRNA. Methods of decreasing expression of Elk-1 mRNA include, but are not limited to, methods that use siRNA, antisense, ribozymes and other specific inhibitors of Elk-1 mRNA expression to inhibit Elk-1 expression.

In a preferred embodiment, siRNA is used to decrease the level of Elk-1 protein. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., 1998, Nature 391(19):306-311; Timmons et al., 1998, Nature 395:854; Montgomery et al., 1998, TIG 14(7):255-258; David R. Engelke, Ed., RNA Interference (RNAi) Nuts & Bolts of RNAi Technology, DNA Press, Eagleville, Pa. (2003); and Gregory J. Hannon, Ed., RNAi A Guide to Gene Silencing, Cold Spring Harbor Laboratory Press, Cold Spring Harbor, N.Y. (2003). Soutschek et al. (2004, Nature 432:173-178) describe a chemical modification to siRNAs that aids in intravenous systemic delivery. Optimizing siRNAs involves consideration of overall G/C content, C/T content at the termini, Tm and the nucleotide content of the 3' overhang. See, for instance, Schwartz et al., 2003, Cell, 115:199-208 and Khvorova et al., 2003, Cell 115:209-216. Therefore, the present invention also includes methods of decreasing levels of Elk-1 protein using RNAi technology.

Inhibitors and activators of Elk-1 expression can be identified by screening test compounds. For instance, inhibitors of endogenous Elk-1 gene expression or of Elk-1 mRNA expression can be identified by screening test compounds for their capacity to reduce or preclude Elk-1 gene expression or Elk-1 mRNA expression in a dendrite or a neuron. Preferably the Elk-1 mRNA is dendritically localized Elk-1 mRNA. The Elk-1 coding sequence in such screening assays may include an in-frame fusion of a tag to the Elk-1 coding sequence. Such tags enable monitoring of Elk-1 expression by antibody detection of the tags or spectral methods of detection (e.g., fluorescence or luminescence).

Test compounds for use in such screening methods can be small molecules, nucleic acids, peptides, peptidomimetics and other drugs. The test compounds of the present invention can be obtained using any of the numerous approaches in combinatorial library methods known in the art, including biological libraries, spatially-addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam, 1997, Anticancer Drug Des. 12:145). Inhibitors and activators of Elk-1 expression may be useful in therapeutic applications, or serve as lead drugs in the development of therapeutics.

Elk-1 protein levels can also be reduced by expression in a neuron of an intrabody directed against Elk-1 protein expressed by an expression vector. Expression vectors and methods of transfecting a neuron with expression vectors are discussed elsewhere herein. Alternatively, an RNA encoding an intrabody directed against Elk-1 protein can be introduced locally into a dendrite using the photoporation method disclosed herein.

Cell viability can be assayed by any method known to the skilled artisan. Methods for assessing cell viability include, but are not limited to, morphological changes, such as pycnotic nuclei, uptake of dyes such as Hoechst dye and trypan blue exclusion. A commercially available kit, LIVE/DEAD cell viability/cytotoxicity kit (Invitrogen Molecular Probes, Carlsbad, Calif.), relies on a membrane permeant esterase substrate that, when cleaved by an esterase in live cells, yields a fluorescent signal.

As also shown herein, modulating the level of Elk-1 protein in a neuron alters the ATP level in the neuron. Specifically, increasing the level of Elk-1 protein causes a decrease in ATP level in a neuron. The inverse is also true, i.e., decreasing the level of Elk-1 protein causes an increased in ATP level in a neuron. As shown in the Examples presented herein, decreasing the ATP level in a neuron increases the susceptibility of the neuron to cell death. Methods of increasing or decreasing Elk-1 protein levels in a neuron are discussed elsewhere herein. ATP levels can be assayed by any method know to the skilled artisan. An exemplary method is a bioluminescent assay employing a luciferase/luciferin enzyme/substrate reaction. Kits for such assays are commercially available, for instance, from Promega.

Altering Specific Activity of Elk-1 Protein

The present invention provides a method of altering dendrite competence and/or viability of a neuron by altering the specific activity of Elk-1 protein, preferably dendritically localized Elk-1 protein. Increasing the specific activity of Elk-1 protein, preferably dendritically localized Elk-1 protein, decreases the dendrite competence and/or viability of the neuron, and also decreases the ATP level in a neuron. Likewise, decreasing the specific activity of Elk-1 protein, preferably dendritically localized Elk-1 protein, increases dendrite competence and/or neuronal viability, and also increases the ATP level in a neuron. Elk-1 specific activity can be altered directly or indirectly.

Increasing the specific activity of Elk-1 protein directly can be accomplished by administering to the dendrite or neuron an amplifier of Elk-1 specific activity. As used herein, an "amplifier of Elk-1 specific activity" refers to a compound that increases the specific activity of Elk-1, preferably dendritically localized Elk-1 protein, by altering the post-translational modification of Elk-1.

Decreasing the specific activity of Elk-1 protein directly can be accomplished by administering an attenuator of Elk-1 specific activity to the dendrite or neuron. As used herein, an "attenuator of Elk-1 specific activity" refers to a compound that decreases the specific activity of Elk-1 by altering the post-translational modification of Elk-1, preferably dendritically localized Elk-1.

An amplifier or attenuator of Elk-1 specific activity may act directly or indirectly. Indirect action, for instance, includes altering the expression an enzyme involved in the post-translation modification. An amplifier or attenuator may act on Elk-1 that is already localized in a dendrite, or on Elk-1 that is subsequently localized in the dendrite.

Elk-1 protein undergoes at least two types of post-translational modification, SUMOylation and phosphorylation, that affect compartmentalization and transcriptional activity of Elk-1. The specific activity of Elk-1 is impacted by both compartmentalization and transcriptional activity of Elk-1. Therefore, alterations to either or both SUMOylation or phosphorylation of Elk-1 affect the specific activity of Elk-1 and, in turn, the competence of a dendrite and/or viability of a neuron. Similarly, alterations to either or both SUMOylation or phosphorylation of Elk-1 affect the ATP level of a neuron.

SUMOylation refers to the covalent attachment of SUMO to lysine residues in target proteins. SUMO is a small peptide, structurally related to ubiquitin, and of similar size (molecular masses are 11 and 9 kDa, respectively). Three SUMO family members, SUMO-1/Smt3C, SUMO-2/Smt3A and SUMO-3/Smt3B, are known to exist in mammals. In SUMOylation, the target lysine generally falls within a recognizable consensus, namely Z-Lys-X-Glu (where Z is a large hydrophobic amino acid, most commonly isoleucine or valine, and X is any residue). SUMOylation involves three enzymatic steps. While not wishing to be bound by theory, it is believed that SUMOylation of dendritically localized Elk-1 decreases its transport into the nucleus, and thereby reduces the nuclear activity of Elk-1, and thus decreasing the specific activity of Elk-1. Thus, any compound that increases the SUMOylation of Elk-1, preferably dendritically localized Elk-1, thus decreases the specific activity of Elk-1 and increases dendrite competence and/or the viability of the neuron. Such a compound thus acts as an attenuator of Elk-1 specific activity. Similarly, any compound that decreases the SUMOylation of Elk-1, preferably dendritically localized Elk-1, thus increases the specific activity of Elk-1 and decreases the competence of the dendrite and/or neuron viability. Such a compound therefore acts as an amplifier of Elk-1 specific activity.

Elk-1 is phosphorylated at multiple S/T residues by MAPK/ERK kinases. While not wishing to be bound by theory, it is believed that phosphorylation of Elk-1 increases the transport of Elk-1 into the nucleus and also increases transcriptional activation by Elk-1, thus increasing the specific activity of Elk-1. Any compound that increases phosphorylation of Elk-1 therefore can act as an amplifier of specific activity. Likewise, inhibition of phosphorylation decreases Elk-1 nuclear activity by decreasing transport into the nucleus and decreasing its transcriptional activity, thereby increasing dendrite competence and/or neuron viability. Any compound that decreases phosphorylation of Elk-1 therefore acts as an attenuator of Elk-1 specific activity. Inhibitors of Elk-1 phosphorylation, and therefore of Elk-1 specific activity, include inhibitors of the MEK/ERK cascade. MEK/ERk inhibitors useful in the instant invention include, but are not limited to, SL327, PD98059, U0126 and 5-iodotubercidin.

Increasing or decreasing SUMOylation or phosphorylation of Elk-1 protein can be accomplished by methods known to the skilled artisan. For instance, to increase either post-translational modification, the amount of one or more of the enzymes involved in the post-translational process can be increased. Such an increase can be accomplished by increasing expression of an endogenous gene for the enzyme, expressing a heterologous gene for the enzyme, increasing the amount, stability or half-life of the mRNA encoding the enzyme, decreasing the degradation of the enzyme or increasing its enzymatic activity. Likewise, the skilled artisan knows methods of decreasing post-translational modification.

The skilled artisan can identify compounds that increase or decrease the post-translation modification of Elk-1 by screening test compounds using assay methods known to the skilled artisan. Screening assays may be in in vitro, using a purified Elk-1, or in vivo. Assays may assess changes in post-translation modification directly, or indirectly. For instance, an assay may rely on changes in the specific activity of Elk-1 as a measure of post-translation modification. Sources of test compounds for screening are disclosed elsewhere herein.

The specific activity of Elk-1 can also be altered indirectly by increasing or decreasing mitochondrial PTP opening. Increasing or decreasing mitochondrial PTP opening can be achieved by administering activators or inhibitors of mitochondrial PTP opening. Inhibiting mitochondrial PTP opening prevents or reduces Elk-1 mediated diminution of dendritic competence or reduction in neuronal viability, thus the specific activity of Elk-1 is decreased. Likewise, activating mitochondrial PTP opening induces Elk-1 mediated diminution of dendritic competence or reduction in neuronal viability, thus the specific activity of Elk-1 is increased. Non-limiting examples of mitochondrial PTP inhibitors include bongkrekic acid, metformin, EGTA, cyclosporin A and tamoxifen. Non-limiting examples of mitochondrial PTP activators include genistein, glutamate, rotenone and carbonyl cyanide m-chlorophenylhydrazone (CCCP).

Other inhibitors and activators of mitochondrial PTP can be identified by assays known to the skilled artisan. Compounds known or suspected of being mitochondrial inhibitors and activators can be tested for the ability to decrease or increase Elk-1 specific activity, respectively, in neuronal cells. Such assays may be performed using individual neurons or population of neurons in culture or using an in vivo assay system. Assays can comprise assessing dendritic competence or neuronal viability after increasing the level of Elk-1 in a dendrite, for instance by photoporating Elk-1 mRNA into a dendrite, in the presence and absence of the test compound. Methods of assessing dendritic competence or neuronal viability are discussed elsewhere herein. Neuronal viability can be assessed for individual neurons or for a population of neurons. Sources of test compounds for screening are disclosed elsewhere herein. Inhibitors of mitochondrial PTP opening that decrease Elk-1 specific activity are candidates as therapeutic agents in alleviating and treating neurodegenerative diseases.

The specific activity of Elk-1 can also be altered indirectly by increasing or decreasing the transcriptional activity of Elk-1 transported from a dendrite to the nucleus. Elk-1 translated in a dendrite or Elk-1 that functionally mimics dendritically translated Elk-1, when transported to the nucleus, induces neuronal cell death, a process that requires the transcriptional activity of Elk-1. Compounds that affect the transcriptional activity of Elk-1, therefore, can affect Elk-1 specific activity. For instance, an inhibitor of Elk-1 transcriptional activity reduces the capacity of Elk-1 to induce neuronal cell death.

Inhibitors and activators of Elk-1 transcriptional activity can be identified using in vitro or in vivo assays or combinations thereof known to the skilled artisan. For instance, inhibitors of Elk-1 transcriptional activity can be identified using purified Elk-1 and an in vitro transcription assay. Alternatively, they can be identified in vivo using, for instance, a recombinant host cell that has a reporter gene for Elk-1 transcriptional activity.

Compounds known or suspected of being Elk-1 transcriptional activity inhibitors and activators can be tested for their ability to decrease or increase Elk-1 specific activity, respectively, in neuronal cells, as described above. Sources of test compounds for screening are disclosed elsewhere herein. Inhibitors of the transcription activity of Elk-1 transported into the nucleus from a dendrite are candidates as therapeutics in alleviating and treating neurodegenerative diseases.

Treatment and Alleviation of a Neurodegenerative Disease

Reduction of the level or specific activity of Elk-1 protein increases neuronal viability. The present invention therefore provides a method for the treatment of a neurodegenerative disease in an individual, accomplished by decreasing the level or specific activity of Elk-1 protein, preferably dendritically localized Elk-1 protein. Methods of decreasing the level or specific activity of Elk-1 protein described elsewhere herein are applicable in the treatment method.

The invention also provides a method of alleviating a neurodegenerative disease in an individual by administering a neuroprotectant that alters the post-translational modification of Elk-1 protein, preferably dendritically localized Elk-1 protein. As discussed elsewhere herein, reduction of the specific activity of Elk-1 protein increases neuronal viability, thereby alleviating neurodegenerative diseases. Thus, the neuroprotectant for use in the practice of this method is an attenuator of Elk-1 protein specific activity.

The therapeutic methods of the invention thus encompass the use of pharmaceutical compositions of an appropriate small molecule, protein or peptide and/or isolated nucleic acid to practice the methods of the invention. The pharmaceutical compositions useful for practicing the invention may be administered to deliver a dose of between 1 ng/kg/day and 100 mg/kg/day. In one embodiment, the invention envisions administration of a dose which results in a concentration of the compound of the present invention between 1 µM and 10 µM in a mammal.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in micro-crystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

Risk of Neuronal Degeneration

The present invention further provides a method for monitoring risk of degeneration by monitoring the level or specific activity of dendritically localized Elk-1 over time. Monitoring neurodegeneration risk may also be done on a population of neurons. Monitoring neurodegeneration risk is useful, for instance, in therapeutic settings. For example, an increased risk of neurodegeneration may allow for prophylactic intervention to prevent or delay the predicted neurodegeneration.

Detecting the level or specific activity of Elk-1 protein in a dendrite may be accomplished by any method for detecting a cellular protein known to the skilled artisan. A preferred method for detecting the level of dendritically localized Elk-1 protein is an immunocytohistological method, presented herein in the Examples, using an antibody directed against Elk-1 protein. Detecting the level of specific activity of Elk-1 protein in a dendrite may be accomplished using antibodies against differently modified forms of Elk-1. For instance, one may use an antibody specific for an Elk-1 protein that has a specific phosphorylation pattern, and associated specific activity, to detect that particular form of Elk-1. In another embodiment, at least two antibodies are used, specific for different forms of Elk-1 having different specific activities. The relative amounts of the two forms may be used to monitor risk of neurodegeneration. Methods for preparing antibodies are presented elsewhere herein.

In one embodiment, the level or specific activity of Elk-1 is detected in a dendrite of a neuron at least twice. The at least two detections are preferably separated in time by at least about 24 hours. If the second level or specific activity of Elk-1 is greater than the first level or specific activity of Elk-1, the neuron is at an increased risk of degeneration and increased susceptibility to neuronal cell death. In another embodiment, the level or specific activity of Elk-1 is monitored in a population of neurons. For instance, using an antibody specific for Elk-1 having an increased specific activity, one can monitor, as a function of time, the level of this protein in neuronal tissue or a bodily fluid, such as cerebrospinal fluid (CSF) or blood, that contacts neuronal tissue. An increase in the level of Elk-1 having an increased specific activity is indicative of an increased risk of neuronal degeneration for the population of neurons.

Isolating a Protein of Mitochondrial PTP

The invention further provides methods of isolating a protein of mitochondrial PTP. As shown herein in the examples, Elk-1 is associated with mitochondrial PTP. Thus, proteins of mitochondrial PTP can be rapidly isolated from a biological sample by co-immunoprecipitating them with Elk-1 using antibodies against Elk-1. Preferably, the antibodies are against dendritically localized Elk-1, which may or may not differ from Elk-1 found elsewhere in a neuron, for instance, in post-translation modifications. Preferred proteins isolated using this method include: adenine nucleotide transporter (ANT), voltage-dependent anion channel (VDAC), ubiquitous mitochondrial creatine kinase (uMTCK) and hexokinase (HXK).

The biological sample used in the practice of this method can be any neuronal tissue. Preferred biological samples for use in this method include brain tissue, synaptoneurosomes or a mitochondrial fraction from fractionated neuronal tissue, as described herein in the examples.

Antibodies directed against Elk-1 are made using methods known to the skilled artisan, and are summarized as follows.

The generation of polyclonal antibodies is accomplished by inoculating the desired animal with the antigen and isolating antibodies which specifically bind the antigen therefrom.

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Human monoclonal antibodies may be prepared by the method described in U.S. patent publication 2003/0224490. Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev.

in Immunol. 12(3,4): 125-168) and the references cited therein. Further, the antibody of the invention may be "humanized" using the technology described in Wright et al., (supra) and in the references cited therein, and in Gu et al. (1997, Thrombosis and Hematocyst 77(4):755-759).

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (2001, Molecular Cloning: A Laboratory Manual, Cold Spring Harbor Laboratory Press, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al., (supra).

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222: 581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al., 1995, J. Mol. Biol. 248:97-105).

A preferred method of co-immunoprecipitation is described in the examples herein. See also Harlow et al., (1988, Antibodies: A Laboratory Manual, Cold Spring Harbor Laboratory Press, Cold Spring Harbor, N.Y.) and Harlow et al., (1999, Using Antibodies: A Laboratory Manual, Cold Spring Harbor Laboratory Press, Cold Spring Harbor, N.Y.).

The instant invention also provides a composition comprising isolated Elk-1 protein and at least one isolated mitochondrial PTP protein. In one aspect, the mitochondrial PTP protein is selected from the group consisting of adenine nucleotide transporter (ANT), voltage-dependent anion channel (VDAC), ubiquitous mitochondrial creatine kinase (uMTCK) and hexokinase (HXK). Most preferably, the mitochondrial PTP protein is ANT.

The composition is useful, for instance, in screening for inhibitors of the association of Elk-1 with the mitochondrial PTP. Such inhibitors are useful in studying the role of the association of dendritically localized Elk-1 with the mitochondrial PTP in dendrite and neuronal viability. Such inhibitors may also be useful in modulating dendrite competence and/or neuron viability, or ATP level, resulting from inhibiting the association of dendritically localized Elk-1 with the mitochondrial PTP in dendrites, thereby having therapeutic potential. Alternatively, the method of isolating at least one mitochondrial PTP protein is readily adapted by the skilled artisan to screen for inhibitors.

Kits

The invention also provides a kit useful in practicing the method of isolating at least one mitochondrial PTP protein. The kit comprises a sample container for holding a biological sample from which the at least one mitochondrial PTP protein is to be isolated. The kit further comprises an antibody directed against Elk-1 protein and a positive control solution comprising a composition comprising isolated Elk-1 protein and at least one isolated mitochondrial permeability transition pore complex protein. Preferably, the antibody is specific or selective for dendritically localized Elk-1 protein. The kit further comprises an instruction material.

As used herein, an "instructional material" includes a publication, a recording, a diagram, or any other medium of expression which can be used to communicate the usefulness of the kit. The instructional material of the kit of the invention may, for example, be affixed to a container which contains the Elk-1 antibody or the positive control solution or be shipped together with a container which contains the Elk-1 antibody or the positive control solution. Alternatively, the instructional material may be shipped separately from the container with the intention that the instructional material and the other kit components be used cooperatively by the recipient.

Introducing RNA Locally into a Neuron

The invention further provides methods of introducing RNA locally into a neuron and a method of translating an RNA in a dendrite. As used herein, "locally introducing" an RNA refers to introducing RNA into a region of cytoplasm that is not the entirety of the cytoplasm of a neuron. Such a region includes, but is not limited to, a single dendrite. As demonstrated herein in the examples, this method advantageously permits the introduction of a small number of RNA molecules into one or more local sites, permitting the controlled and localized production of protein in physiological amounts. This method thus allows dendritic localization of exogenously applied mRNA without resorting to severing the dendrite from the neuron to which it is attached.

The methods include providing an RNA to a neuron and photoporating the neuron at one or more sites. The neuron is preferably a primary cell culture or in slice culture. The neuron may be photoporated on any site. Preferably, the site is on a dendrite or the cell body. The RNA can be provided to the neuron by any method known to the skilled artisan, and is preferably provided by means of an RNA bath. An RNA bath is a solution comprising the RNA of interest in which the neuron is bathed. The solution is of an appropriate salinity to maintain the structural integrity of the neuron to be photoporated. The RNA of interest may be any size. For instance, RNAs of about 800 nucleotides and RNAs about 3000 nucleotides have been successfully photoporated into neurons using the inventive procedure.

A Ti-sapphire laser is used to photoporate one or more specific sites on a neuron, thereby transiently allowing RNA in the RNA bath to enter the cell at that site. In one embodiment, a neuron is in an RNA bath containing an RNA molecule of about 1000 nucleotides at about 1 to about 45 µg/ml, more preferably about 5 to about 20 µg/ml, and more preferably still at about 10 to about 15 µg/ml in the bath. The neuron is subjected to one to about 30 laser pulses, more preferably about 3 to about 25 laser pulses and more preferably still, about 8 to about 16 laser pulses, each pulse about 5 milliseconds long.

The number of RNA molecules that enter the neuron is influenced by the RNA concentration in the RNA bath, the size of the RNA molecule, and laser intensity, e.g., the length of each laser pulse and the number of laser pulses delivered. Based on the teachings herein, the skilled artisan can readily adjust the parameters of the photoporation process to control the approximate number of RNA molecules that enter the neuron per pulse.

Any coding sequence of interest can be used in the methods of introducing and translating an RNA in a dendrite. One of skill in the art will understand, when armed with the present disclosure, that a multitude of properties of a dendrite, and by association, of a neuron, can be affected by the methods of the present invention. For instance, for studies of dendrite remodeling, any coding sequence for a protein involved in the growth, homeostasis or remodeling of a dendrite are useful in the methods of the invention. Non-limiting examples include: cadherin, neurexin, synaptophysin, tubulin, microtubule associated proteins and actin.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The materials and methods used in the experiments presented in the Experimental Examples below are now described.

Cell culture: Neuron-enriched primary rat hippocampal cultures from E18.5 embryos were plated at 100,000 per ml in Neurobasal medium (Invitrogen, Carlsbad, Calif.) with B-27 supplement (Sigma, St. Louis, Mo.) on 12 mm round German Spiegelglas coverslips (Bellco) or gridded coverslips (Eppendorf), as previously described. For a subset of photoporation experiments (see below), primary rat hippocampal neurons from Cambrex Corporation (East Rutherford, N.J.) were also used.

Immunocytochemistry/immunohistochemistry: Three polyclonal antibodies raised against Elk-1 (Santa Cruz Biotechnology, Santa Cruz, Calif.; Cell Signaling Technology, Beverly, Mass.) were used to detect Elk-1 protein in primary rat hippocampal cultures and in adult rat brain sections. A monoclonal antibody raised against a synthetic phospho-peptide of Elk-1 was used to detect Elk-1 protein phosphorylated at S383 (Cell Signaling Technology). A somatodendritic MAP2 antibody (Craig Garner, Stanford University) was used to confirm dendritic localization of Elk-1. 7-14 day-old cultured neurons were fixed with 4% paraformaldehyde (Electron Microscopy Sciences), permeabilized with 0.2% TritonX-100 in PBS, blocked with 10% normal goat serum (Jackson ImmunoResearch), 1% bovine serum albumin (Sigma) and 0.1% TritonX-100 in PBS, and visualized using Cy3 (Jackson ImmunoResearch) or Alexa488 (Invitrogen Molecular Probes, Carlsbad, Calif.) secondary antibodies. Omission of the primary antibody resulted in an absence of staining (data not shown). For stimulation experiments, cultured neurons were placed in warm Hals buffer (pH=7.4) and treated with the Group I mGluR agonist, dihydrophenylglycine (DHPG; Tocris Cookson Inc., Ellisville, Mo.) at a final concentration of 50 µM for 30 minutes at 37° C. prior to fixation and immunocytochemistry.

In situ hybridization: Full-length Elk-1 was inserted into a pcDNA vector (Invitrogen), which was then used to produce Elk-1 transcripts (Ambion mMessage mMachine®) labeled with digoxigenin (Roche). 400 bp sense and antisense probes were produced by alkaline hydrolysis of the full-length digoxigenin-labeled Elk-1 (see Baldino et al., 1994). 7-14 day-old primary rat hippocampal cultures were fixed in 4% paraformaldehyde, washed in PBS and permeabilized with 0.3% TritonX-100. Cells were pre-hybridized at 42° C. overnight with 50% formamide, 1×Denhardt's solution, 4×SSC, 10 mM DTT, 0.1% CHAPS, 0.1% Tween-20, 500 µg/ul yeast tRNA and 500 µg/ul salmon sperm DNA. Hybridization was performed overnight at 42° C. with 2.5 ng/µl probe in pre-hybridization buffer with the addition of 8% Dextran sulfate. Sheep antidigoxigenin (Roche) followed by alkaline phosphatase was used for probe visualization.

Elk-1 Translation: Full-length Elk-1 and a c-myc epitope sequence were inserted into a TOPO vector (Invitrogen) with the c-myc epitope sequence in-frame at the C-terminus of Elk-1. This construct was then used to generate Elk-1 c-myc RNA in vitro (Ambion mMessage mMachine®). Dendrites from primary rat hippocampal neurons, plated on gridded glass coverslips (Eppendorf), were mechanically isolated using a glass micropipette tip, and the cell body was removed. C-myc tagged Elk-1 RNA coated in lipids (Lipofectamine™ 2000, Invitrogen) was immediately blown onto the isolated dendrites. The isolated dendrites were then treated with DHPG at a final concentration of 50 µM for 30 minutes at 37° C. to stimulate translation, and processed for c-myc immunoreactivity.

Synaptoneurosome and mitochondrial fractionation for co-immunoprecipitation: Synaptoneurosome isolation was based on the established technique of Booth and Clark (1978). Briefly, 6-8 week old male C57BL/6 mice were sacrificed by $CO_2$ followed by cervical dislocation. After removal of the cerebellum, the brain was homogenized with a large dounce homogenizer (Wheaton) in cold isolation medium containing: 320 mM Sucrose, 10 mM Tris-HCl and 1 mM EDTA. The homogenate was spun at 3,500 rpm for three minutes, and the supernatant collected and re-spun at 10,000 rpm for ten minutes. After re-suspension of the pellet in cold isolation medium, the solution was further homogenized and mixed with 12% Ficoll (Sigma). 7% Ficoll and isolation medium were layered on the homogenate, and solutions were spun at 27K RPM for 35 minutes (Beckman L8-55M). Synaptoneurosome fractions (SN) collected between the 12% and 7% Ficoll layers, and mitochondrial fractions (MT) collected at the base of the tube, were used immediately for co-immunoprecipitation.

Co-immunoprecipitation (co-IP): Mouse whole brain (WB), synaptoneurosome (SN) and mitochondrial (MT) fractions were lysed in the presence of protease inhibitors under non-denaturing conditions, pre-cleared with Protein A Agarose (Invitrogen) and immunoprecipitated with one of two polyclonal Elk-1 antibodies (Santa Cruz Biotechnology). Lysis buffer contained: 50 mM Tris HCl, 150 mM NaCl, 0.5% TritonX-100, 0.5% octyl-β-D1-thioglucopyranoside, 10 µg/mL Aprotinin, 5 µg/mL Leupeptin, 1 mM sodium orthovanadate, 1 mM PMSF and 100 µg/mL TPCK. Immunoprecipitates were fractionated by SDS-PAGE, stained with Coomassie Blue, and bands were submitted to the University of Pennsylvania Proteomics Core Facility for peptide sequencing using an LCQ Deca XP Plus mass spectrometer (Thermo Electron Corp., Waltham, Mass.). Reciprocal co-IP from WB, SN and MT fractions, using antibodies against hexokinase (HXK; Chemicon International, Temecula, Calif.), voltage dependent anion channel (VDAC; Santa Cruz Biotechnology), adenine nucleotide transporter (ANT; Santa Cruz Biotechnology) and ubiquitous mitochondrial creatine kinase (UMTCK; Santa Cruz Biotechnology) followed by Western blotting with an Elk-1 antibody (Cell Signaling Technology), was carried out on binding partners detected through peptide sequencing. Protein lysates were run on NuPAGE 10% Bis-Tris precut gels (Invitrogen), transferred to PVDF membrane (BioRad), stained with primary antibody and visualized using chemiluminescence (Perkin Elmer).

Electron microscopy: 250 g male rats (n=3) were anesthetized with sodium pentobarbital (60 mg/kg) and perfused transcardially with 50 ml of 3.8% acrolein (Electron Microscopy Sciences, Fort Washington, Pa.) and 200 ml of 2% paraformaldehyde in 0.1 M phosphate buffer (PB; pH 7.4). The brains were removed, cut into 1-3 mm coronal slices and post-fixed for an additional 30 minutes. Sections (40 µm) were cut through the rostrocaudal extent of the hippocampal formation using a Vibratome and collected into 0.1 M PB. These were placed in 1% sodium borohydride to remove reactive aldehydes and rinsed in 0.1 M PB before the primary antibody incubation. The sections were incubated in an Elk-1 antibody (Cell Signaling Technology) for 15-18 hours at room temperature. Control sections were run in parallel in which the primary antisera was omitted, but the rest of the processing procedure was identical. Sections were rinsed in 0.1 M phosphate buffered saline (PBS) and incubated in the secondary antiserum at room temperature. For peroxidase detection of Elk-1, sections were incubated in biotinylated donkey anti-rabbit IgG (1:400; Jackson Immunoresearch, West Grove, Pa.) for 30 minutes, followed by incubation in avidin-biotin complex (Vector Laboratories, Burlingame, Calif.). This was visualized by reaction with 3-3' diaminobenzidine (Aldrich, St. Louis, Mo.) and H2O2 in 0.1 M PBS. For immunogold-silver detection of Elk-1, sections were incubated in 0.01 M PBS containing 0.1% gelatin and 0.8% bovine serum albumin (BSA) for 30 minutes. Sections were then incubated in donkey anti-rabbit IgG conjugated to 1 nm gold particles (Amersham Corp., Piscataway, N.J.) for 2 hours at room temperature. These were rinsed and incubated in 1.25% glutaraldehyde (Electron Microscopy Sciences, Fort Washington, Pa.), followed by a wash in 0.01 M PBS and then in 0.2 M sodium citrate buffer (pH 7.4). Silver intensification of the gold particles was achieved using a silver enhancement kit (Amersham Corp.). Sections were rinsed and incubated in 2% osmium tetroxide (Electron Microscopy Sciences) for 1 hour, rinsed, dehydrated and flat embedded in Epon 812 (Electron Microscopy Sciences). Thin sections (80-100 nm) were cut from the outer surface of the tissue, collected on grids and examined with an FEI transmission electron microscope.

Mitochondrial fractionation for western blots: A mitochondrial isolation kit (Pierce) was used according to the manufacturer's instructions to isolate mitochondria from primary neuronal cultures. Once isolated, mitochondria were lysed in buffer containing: 150 mM NaCl, 1% NP-40, 0.5% Deoxycholic acid, 0.1% SDS, 50 mM Tris, 10 ug/mL Aprotinin, 5 ug/mL Leupeptin, 1 mM sodium orthovanidate, 1 mM PMSF and 100 ug/mL TPCK. Lysate was then used for western blotting with the following antibodies: Elk-1 (Cell Signaling Technology), VDAC 1 (Santa Cruz Biotechnology), NeuN (Abcam).

ATP cell viability measurements: Elk-1 in a pcDNA mammalian expression vector (Invitrogen), Elk-1 siRNA (Ambion pre-designed siRNA) or Silencer™ Negative Control siRNA (Ambion, Austin, Tex.) was introduced into primary rat hippocampal neurons in suspension using electroporation according to the manufacturer's instructions (Amaxa Biosystems, Gaithersburg, Md.). Two different Elk-1 siRNAs were introduced, corresponding to different regions of Elk-1 (siRNA A target sequence: GGTGAGCGGCCAGAAGTTT, SEQ ID NO: 4, siRNA B target sequence: AGTTGGTGGAT-GCAGAGGA, SEQ ID NO: 5). Neurons were then plated on glass coverslips, and a luminescent cell viability assay (Promega) was used to detect total cellular ATP levels 24, 48, 72, 96 and 168 hours after plating. Neurons were lysed with CellTiter-Glo® reagent (Promega), equilibrated at room temperature for 30 minutes, and luminosity was measured with a spectrofluorometer (Tecan, Durham, N.C.).

Cell Counts: Following electroporation of plasmid Elk-1 or Elk-1 siRNA, cells were stained with a neuron specific MAP2 antibody 24, 48, 72, 96 and 168 hours after plating. Two 5× images were taken from identical regions on each coverslip, and MAP2-positive neurons were counted manually.

Photoporation: The following capped mRNAs were synthesized for use in the photoporation experiments (Ambion mMessage mMachine®): GFP-tagged Elk-1, GFP (Clontech), DS-RED (Clontech), Venus-CFP (mutated EYFP cloned in the Haydon lab), pTRI-Xef (Ambion) and Elk-1-ETS. Elk-1-ETS contains Elk-1 with the initiator methionine but without its DNA binding domain. It was PCR generated and sequence verified. Cultured primary rat hippocampal neurons were bathed in 10-15 µg capped mRNA in 1 ml extracellular saline at 37° C. In some cases, neurons were pre-incubated with the translation inhibitor, anisomycin (5 µM), the mitochondrial PTP inhibitor, bongkrekic (BKA; 25 µM), or the transcriptional inhibitor, actinomycin D (1 µg/ml). BKA has been used in primary neuronal culture in concentrations ranging from 2 µM to 50 µM to inhibit PTP opening and to demonstrate the mitochondrial dependence or independence of cell death pathways (Hans et al., 2005, Neuropharmacology 48:105-117; Jiang et al., 2001, J. Biol. Chem. 276:47524-47529; Tang et al., 2005, PNAS 102:2602-2607; and Jordan et al., 2003, Neuroscience 122:707-715).

Samples were imaged and photoporated using a Prairie Ultima multiphoton scan head attached to an Olympus BX61 fixed-stage upright microscope equipped with a 40× water immersion lens (LUMPlanFI/IR, N.A. 0.8). 8 to 16 points were selected over a 2 µm×2 µm area for photoporation. A Ti-sapphire laser (Mai-Tai®, Spectral-Physics, Mountain View, Calif.) was used to make transient poration sites for 5 milliseconds at 30 mW (at back aperture of lens) energy. After photoporation, samples were transferred to an Olympus IX81 inverted microscope for simultaneous GFP fluorescence and DIC imaging. All images were processed with Metamorph (Universal Imaging Corporation) image processing software. For cell death assays, a LIVE/DEAD cell viability/cytotoxicity kit (Molecular Probes) was used according to the manufacturer's instructions.

Experimental Example 1

Elk-1 Protein is Localized in Dendrites and can be Dynamically Regulated by mGluR Stimulation Immunocytochemistry on primary rat hippocampal neurons (FIG. 1), and immunohistochemistry on rat brain sections (data not shown) revealed Elk-1 immunoreactivity in both proximal and distal dendrites. Co-staining with a somatodendritic MAP2 antibody was used to confirm Elk-1's dendritic localization. This pattern of staining was seen with multiple antibodies and is consistent with previous reports by Sgambato et al. (1998, The Journal of Neuroscience 18: 214-226) of Elk-1 immunoreactivity in dendrites. Immunoreactivity for both Elk-1 (FIG. 1A) and Elk-1 phosphorylated at S383 (FIG. 1C) could be seen in proximal and distal dendrites, indicating that dendrites also contain post-translationally modified versions of Elk-1. After a 30-minute application of DHPG (50 µM), which increases translation through stimulation of Group I mGluRs (Raymond et al., 2000), there was a substantial increase in Elk-1 immunoreactivity in both cell somas and dendrites (n=7; FIG. 1B), suggesting that Elk-1 protein abundance can be rapidly and dynamically regulated in both sub-cellular compartments.

Experimental Example 2

Elk-1 mRNA is Localized in Dendrites and can be Locally Translated

Figures 2A, 2B, 2C:
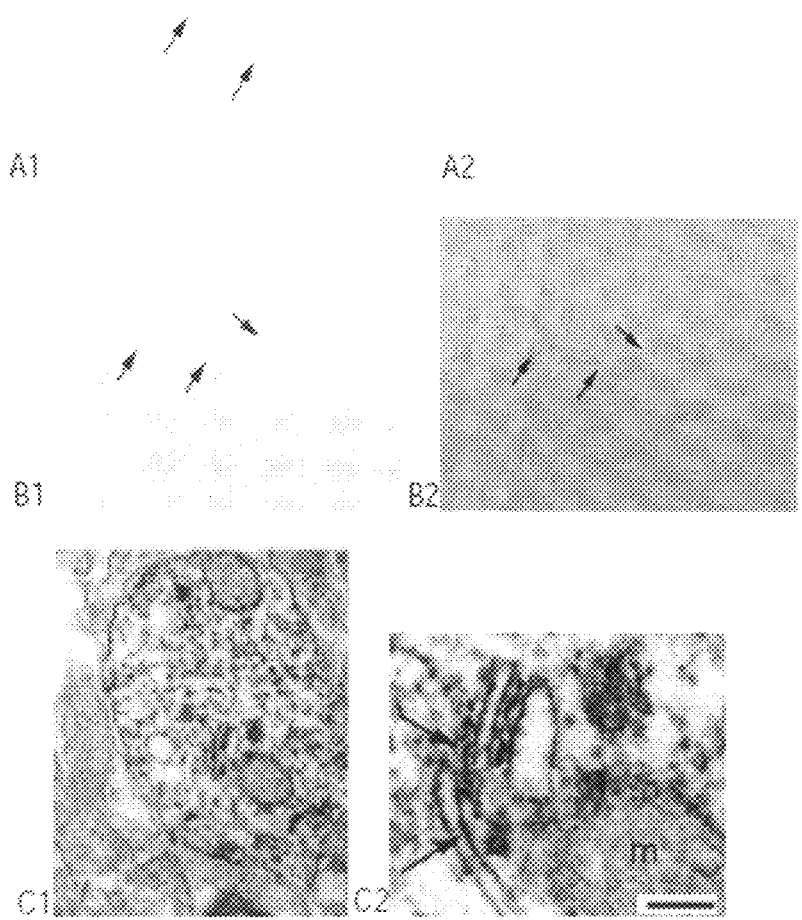
FIG. 2A depicts in situ hybridization on primary rat hippocampal neurons using 2.5 μg/μl 400 bp digoxigenin-labeled antisense (A1) and sense (A2) Elk-1 RNA probes, followed by alkaline phosphatase for probe visualization. Arrows indicate alkaline phosphatase signal in both proximal and distal dendrites.
FIG. 2B depicts c-myc immunoreactivity in isolated dendrites (B1) of neurons onto which c-myc tagged Elk-1 mRNA was blown. B2 shows the phase image of dendrites in B1 after the cell body has been removed.
FIG. 2C depicts immunoperoxidase labeling of Elk-1 (arrows) in adult rat brain sections. C2 shows a magnified view of the endoplasmic reticulum shown in C1. Scale bar=100 nm.

Using in situ hybridization, endogenous Elk-1 mRNA was localized in dendrites. 400 bp sense and antisense digoxigenin-labeled Elk-1 RNA probes were hybridized to primary rat hippocampal neurons and visualized with alkaline phosphatase. FIG. 2A shows alkaline phosphatase signal present with application of the antisense probe (n=3; FIG. 2A1) and absent with application of the sense control (n=3; FIG. 2A2). Note that alkaline phosphatase signal can be seen in both proximal and distal dendrites. While RNA localization in dendrites is suggestive of local translation, it is not proof of local translation. In order to assess whether Elk-1 mRNA can be translated in dendrites, an isolated dendrite assay was used as previously described (Crino et al., 1996, Neuron 17: 1173-1187; Kacharmina et al., 2000, Proc. Natl. Acad. Sci. USA 97: 11545-11550; Job and Eberwine, 2001, Proc. Natl. Acad. Sci. USA 98:13037-13042). Briefly, mRNA with an in-frame c-myc epitope tag sequence in the C-terminus of the coding region of Elk-1 was transcribed from a reporter cDNA. After mechanical isolation of individual cultured dendrites, lipid-coated c-myc tagged Elk-1 mRNA was blown onto isolated dendrites. After 30 minutes at 37° C., DHPG (50 µM) was applied to stimulate translation, and 30 minutes later, c-myc immunoreactivity was assessed (n=3). C-myc immunoreactivity was detected in isolated dendrites, indicating that Elk-1 mRNA can be locally translated (FIG. 2B). Consistent with this finding, electron microscopy of adult rat brain sections revealed co-localization of immunogold-silver labeling for Elk-1 with endoplasmic reticulum in dendrites (FIG. 2C), showing that Elk-1 protein is associated with translational machinery in dendrites. Local translation of Elk-1 protein would allow for the rapid and dynamic regulation of Elk-1 protein abundance.

Experimental Example 3

Elk-1 Interacts with Several Mitochondrial Proteins that Form the Permeability Transition Pore Complex To investigate the function of dendritically localized Elk-1, its protein binding partners were characterized using co-immunoprecipitation (co-IP) from adult mouse whole brain tissue and synaptoneurosome fractions. Synaptoneurosomes, while not pure preparations, represent fractions enriched in pre- and post-synaptic aspects of neurons and were used to detect potential interactions with low-abundance synaptic proteins. This allowed examination for protein interactions from a primarily synaptic-area in addition to whole-brain lysates. Immunoprecipitates from both fractions were submitted for LCQ peptide sequencing at the University of Pennsylvania Proteomics Core Facility. Co-IP with two Elk-1 antibodies (Santa Cruz Biotechnology), raised against different epitopes, pulled out several mitochondrial proteins from both whole brain and synaptoneurosome fractions. The mitochondrial proteins include the adenine nucleotide transporter (ANT) and voltage-dependent anion channel (VDAC), both integral membrane proteins, and the ubiquitous mitochondrial creatine kinase (uMTCK) and hexokinase (HXK), both enzymes important for energy metabolism (FIG. 3A). All four proteins have been implicated in the functioning of the mitochondrial permeability transition pore complex (PTP) (Beutner et al., 1998, Biochemica et Biophysica Acta 1368: 7-18). The PTP is a protein complex forming a functional pore that, once open, allows molecules up to 1.5 kDa to move across the mitochondrial inner membrane non-selectively (Kim et al., 2003, Biochemical and Biophysical Research Communications 304: 463-470). PTP opening is a critical step in the initiation of apoptotic and necrotic cell death cascades, as it can induce mitochondrial swelling, membrane potential depolarization, ATP hydrolysis and release of stored soluble proteins (Halestrap et al., 2002, Biochemie 84: 153-166).

Figure 3B:
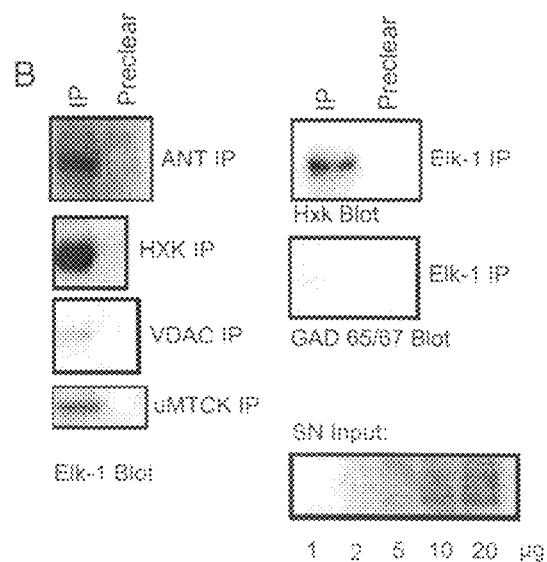
FIG. 3B depicts images of reciprocal co-IPs from synaptoneurosome fractions. Images on the left depict reciprocal co-IP was carried out using antibodies against ANT, VDAC, HXK and uMTCK. Protein fractions were then analyzed by Western blot using an Elk-1 antibody. Images on the right depict reciprocal co-IP using an antibody against Elk-1. Protein fractions were then analyzed by Western blot using antibodies to HXH and GAD65/67. Also shown is the synaptoneurosome (SN) input fraction. Multiple banding pattern is consistent with phosphorylated Elk-1.
Figure 3C:
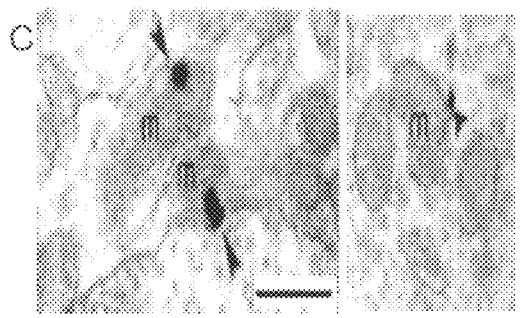
FIG. 3C depicts two images of immunogold-silver labeling of Elk-1 (arrowhead), illustrating its association with mitochondria (m) in a hippocampal dendrite from adult rat brain. Scale bar=500 nm.

Interaction of Elk-1 with these mitochondrial proteins was confirmed through reciprocal co-IP with antibodies against ANT (n=4), VDAC (n=2), hexokinase (n=3) and uMTCK (n=2), followed by Western blotting with an Elk-1 antibody (FIG. 3B). Large bands corresponding to Elk-1 from the ANT immunoprecipitation were found with only 12.5 ng protein lysate, suggesting a high affinity association between Elk-1 and ANT. Immunoprecipitation with an Elk-1 antibody followed by Western blotting with either an HXK antibody or GAD 65/67 antibody were used as positive and negative controls, respectively (FIG. 3B, right hand images).

Experimental Example 4

Elk-1 is Localized Around Mitochondria in Cell Somas and Dendrites

In light of the apparent interaction between Elk-1 and mitochondrial proteins, electron microscopy was used to confirm the mitochondrial localization of Elk-1. Using peroxidase detection and immunogold-silver detection in adult rat hippocampal sections, Elk-1 signal was visualized around mitochondrial membranes in cell somas and dendrites (FIG.

Figure 3D:
FIG. 3D are images of Western blots from purified mitochondrial fractions. There is a signal for Elk-1 and the mitochondrial protein VDAC1 but no signal for the negative control, NeuN.
Figure 3E:
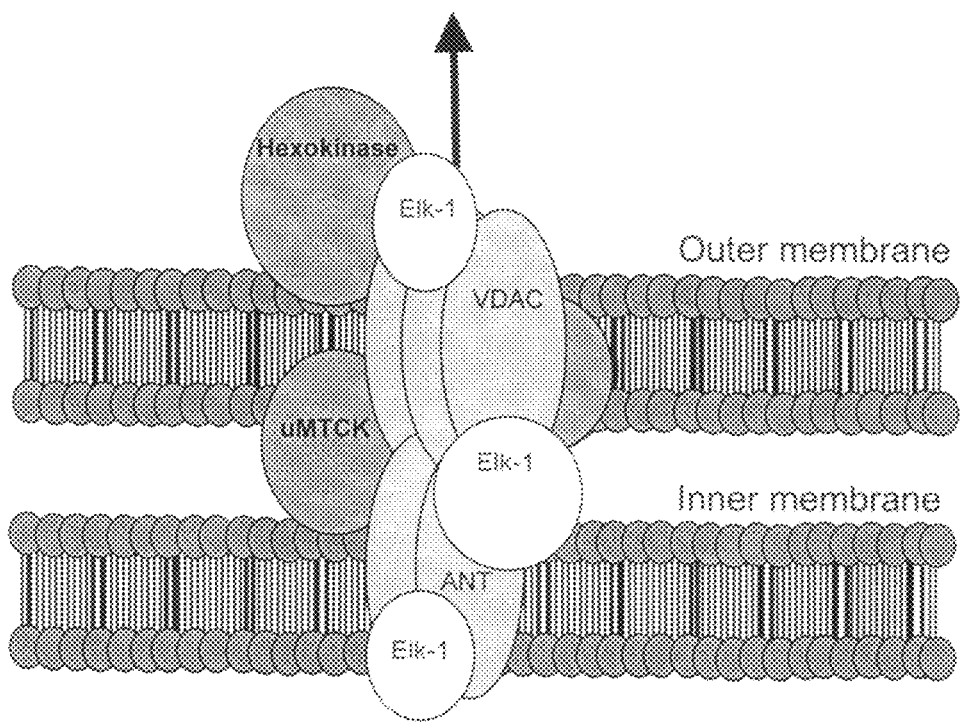
FIG. 3E is a schematic illustration of potential interactions of Elk-1 with proteins that form the mitochondrial PTP.

3C), showing a definitive association of Elk-1 with mitochondria. Elk-1 also blotted from purified mitochondrial fractions (FIG. 3D). Potential sites of interaction between Elk-1 and the inner and outer mitochondrial membranes are shown in FIG. 3E. While the EM data does not allow distinguishing whether Elk-1 interacts directly with proteins on the inner mitochondrial membrane vs. the outer mitochondrial membrane, they do confirm the previous biochemical finding of Elk-1 association with mitochondrial proteins. This is the first demonstration of any association between Elk-1 and mitochondria, a finding that significantly broadens the potential functionality of Elk-1.

To examine whether specific cellular insults could increase or decrease the association between Elk-1 and mitochondria, primary rat corticol neurons were exposed to a variety of compounds known to induce cell death in neurons, and mitochondrial fractions were then isolated and used for Western blotting. Using this paradigm, it was observed that Elk-1 increased its association with mitochondria after application of camptothecin, an inhibitor of topoisomerase I, or etoposide, an inhibitor of topoisomerase II. Both camptothecin and etoposide are known to induce DNA damage and apoptosis in neurons. The observed increase in association could be detected as soon as 3 hours after drug application, consistent with the time course in which DNA damage and subsequent cell death are initiated, and continued to be detected after drug application.

Experimental Example 5

Elk-1 Over-Expression Leads to Decreased ATP Levels and Increased Cell Death Whereas Elk-1 siRNA Leads to Increased ATP Levels and Cell Viability Through its interactions with the mitochondria, it was hypothesized that Elk-1 is able to influence cell viability. To test this hypothesis, primary rat hippocampal neurons were electroporated with either a mammalian expression vector that expresses Elk-1 mRNA, an empty mammalian expression vector without Elk-1 (pcDNA 3.1; control), one of two Elk-1 siRNA, or control siRNA with no signification sequence similarity to the rat genome) to determine the effects of Elk-1 over-expression or knockdown throughout whole cells in culture. Using electroporation, an average transfection efficiency of around 50% was obtained (based on GFP transfections; data not shown), although the exact efficiencies varied with use. All subsequent analysis was performed on mixed cultures that contained both transfected and untransfected neurons. As a result, the findings underestimate the effects of Elk-1 on cell viability.

Figure 4A:
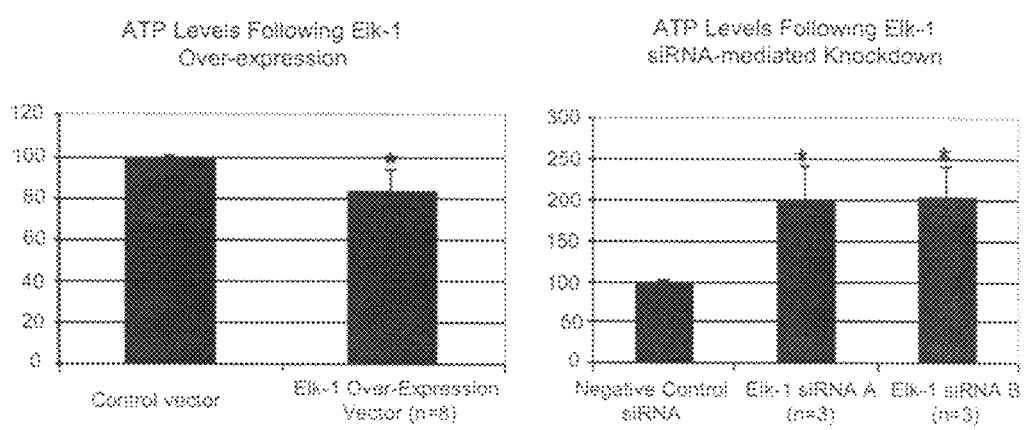
FIG. 4A is a bar graph of the average percent change in ATP levels following electroporation for Elk-1 pcDNA compared to control, and for Elk-1 siRNA compared to control. Elk-1 in a pcDNA vector or pre-designed Elk-1 siRNA was electroporated into primary rat hippocampal neurons in suspension. Whole-cell ATP levels were measured at 24 hours following electroporation using an ATP cell viability assay. (A) The graph on the left shows whole-cell ATP levels from primary rat hippocampal neurons 48 hrs following electroporation with either Elk-1 in a pcDNA3.1 vector or pcDNA3.1 vector alone (control). The graph on the right shows whole-cell ATP levels from primary rat hippocampal neurons 48 hrs following electroporation (Amaxa Biosystems) with either one of two Elk-1 siRNAs (Ambion) or pSilencer Negative Control siRNA (Ambion). ATP levels are normalized to control. Error bars represent standard deviations and * indicates $P<0.05$ when comparing siRNA mediated knockdown to control or Elk-1 over-expression to control.
Figure 4B:
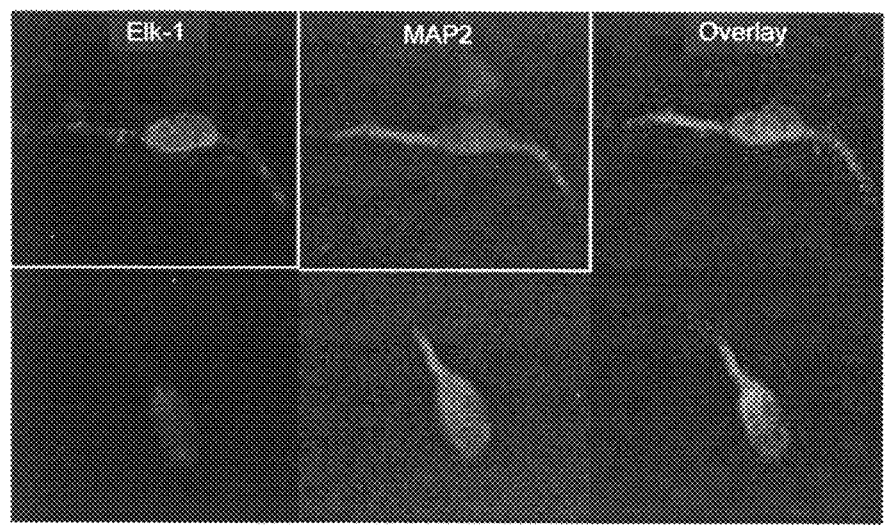
FIG. 4B is a series of images depicting Elk-1 immunoreactivity in culture, examined 24 hours after plating of control neurons (B1) and of neurons electroporated with siRNA (B2). Elk-1 protein was detected using Cy3 and MAP2 protein was detected using Alexa 488. Merged images show immuno-detection of Elk-1 and MAP2.
Figure 4C:
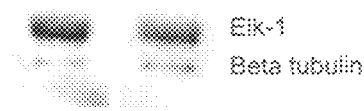
FIG. 4C depicts images of western blots, carried out 24 hours after plating, for control neurons and neurons electroporated with siRNA B to assess siRNA-mediated knockdown of Elk-1 protein expression. The Elk-1 protein level decreases following siRNA-mediated knockdown. Beta tubulin was used as a loading control.
Figure 4D:
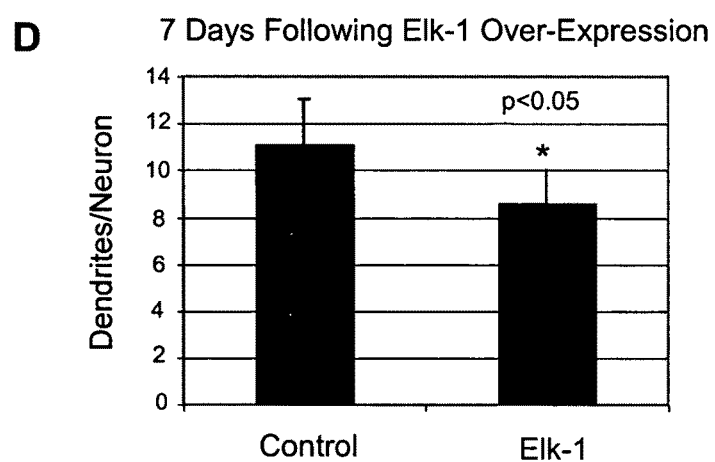
FIG. 4D is a bar graph showing the number of dendrites per neuron following Elk-1 overexpression. Neurons were counted using Neurolucida software and image analysis, 7 days following electroporation with Elk-1 in a pcDNA3.1 vector or a pcDNA3.1 vector alone without Elk-1 (control).

Using a luminescent ATP cell viability assay, a decrease was observed in whole-cell ATP levels 24 hrs after Elk-1 over-expression compared to control (n=8; FIG. 4A). This decrease in ATP levels was maintained over the course of 7 days (data not shown). Conversely, an increase was observed in whole-cell ATP levels 24 hrs following Elk-1 siRNA mediated knockdown compared to control (n=3; FIG. 4A), a finding that was also maintained over the course of 7 days (data not shown). Similar results were observed for both Elk-1 siRNAs. Immunocytochemistry (n=4; FIG. 4B) and Western blots (n=3; FIG. 4C) were used to confirm that Elk-1 siRNA electroporated into primary rat hippocampal neurons decreased Elk-1 protein expression. Consistent with the changes in ATP levels, a decrease in the number of live neurons following Elk-1 over-expression (FIGS. 5A, 5B) with no change in dendrite volume or tortuosity, and an increase in the number of live neurons following Elk-1 siRNA mediated knockdown (data not shown), was observed. The fact that Elk-1 siRNA did not produce detrimental cellular effects is consistent with previous data on Elk-1 knockout mice, which show no obvious behavioral phenotype (Cesari et al., 2004). Interestingly, by seven days after Elk-1 over-expression, a significant decrease in the number of dendrites per neuron in the surviving neurons was observed (FIG. 4D), with no change in dendrite volume or tortuosity (data not shown). Because neurons were electroporated throughout whole cells in suspension, this does not distinguish between a pruning back of already elaborated dendrites, or a failure of initial dendrite outgrowth. Once made, both Elk-1 mRNA and Elk-1 protein were also free to move throughout entire cells.

Figure 5A:
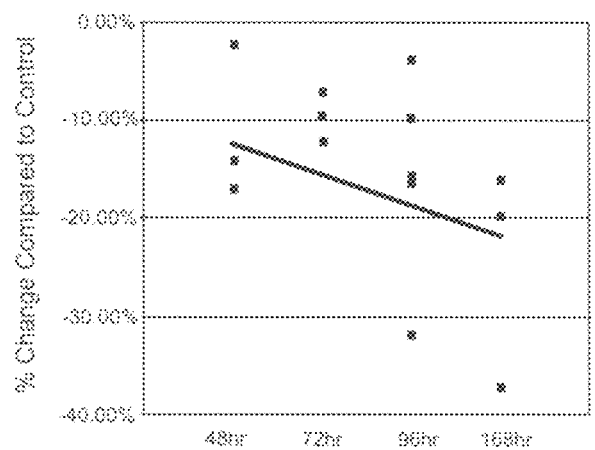
FIG. 5A is a graph depicting cell counts after Elk-1 overexpression. Neurons electroporated with Elk-1 in a pcDNA vector were stained with a MAP2 antibody at 48, 72, 96 and 168 hours after plating. Two 5× images of MAP2 immunoreactive neurons were taken for each experiment, and MAP2 positive neurons were counted manually. Shown are the percent decreases in MAP2 positive neurons compared to control. (Line=best fit) FIG. 5B are images of MAP2 immunoreactivity from neurons electroporated with a control pcDNA vector (right image) or with Elk-1 in pcDNA (left image).
Figure 5B:
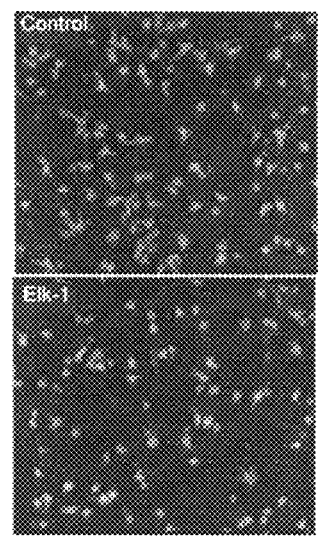
FIG. 5C is a series of images depicting neurons electroporated with Elk-1 stained with either DAPI or Hoechst at 24 hrs and 48 hrs to assess pycnotic nuclei. The third image depicts neurons after a 3 hour treatment with the apoptosis inducer, camptothecin, and shows the presence of the presence of pycnotic nuclei. Scale bar=20 µm.
Figure 5C:
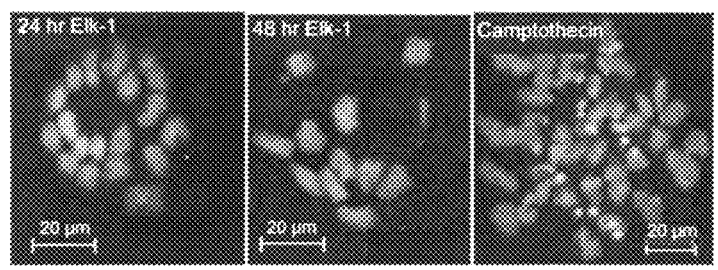

In order to assess whether neurons were dying via apoptosis or necrosis following Elk-1 over-expression, DAPI and Hoechst nuclear stains were used to look for evidence of pycnotic nuclei, characteristic of an apoptotic phenotype. FIG. 5C shows the absence of pycnotic nuclei 24 hrs and 48 hrs following Elk-1 over-expression, compared to the presence of pycnotic nuclei when cells were treated for 3 hours with 30 µM of the apoptosis inducer camptothecin. This suggests that the cells over-expressing Elk-1 were not dying through an apoptotic mechanism, but were more likely undergoing necrosis. Interestingly, following Elk-1 over-expression, some of the neurons displayed changes in dendrite morphology. Specifically, a significant decrease in the number of dendrites per neuron after Elk-1 over-expression was observed (data not shown).

Taken together, these findings indicate an over-abundance of Elk-1 produces cell death and a reduction of Elk-1 enhances cell survival.

Experimental Example 6

Figure 6:
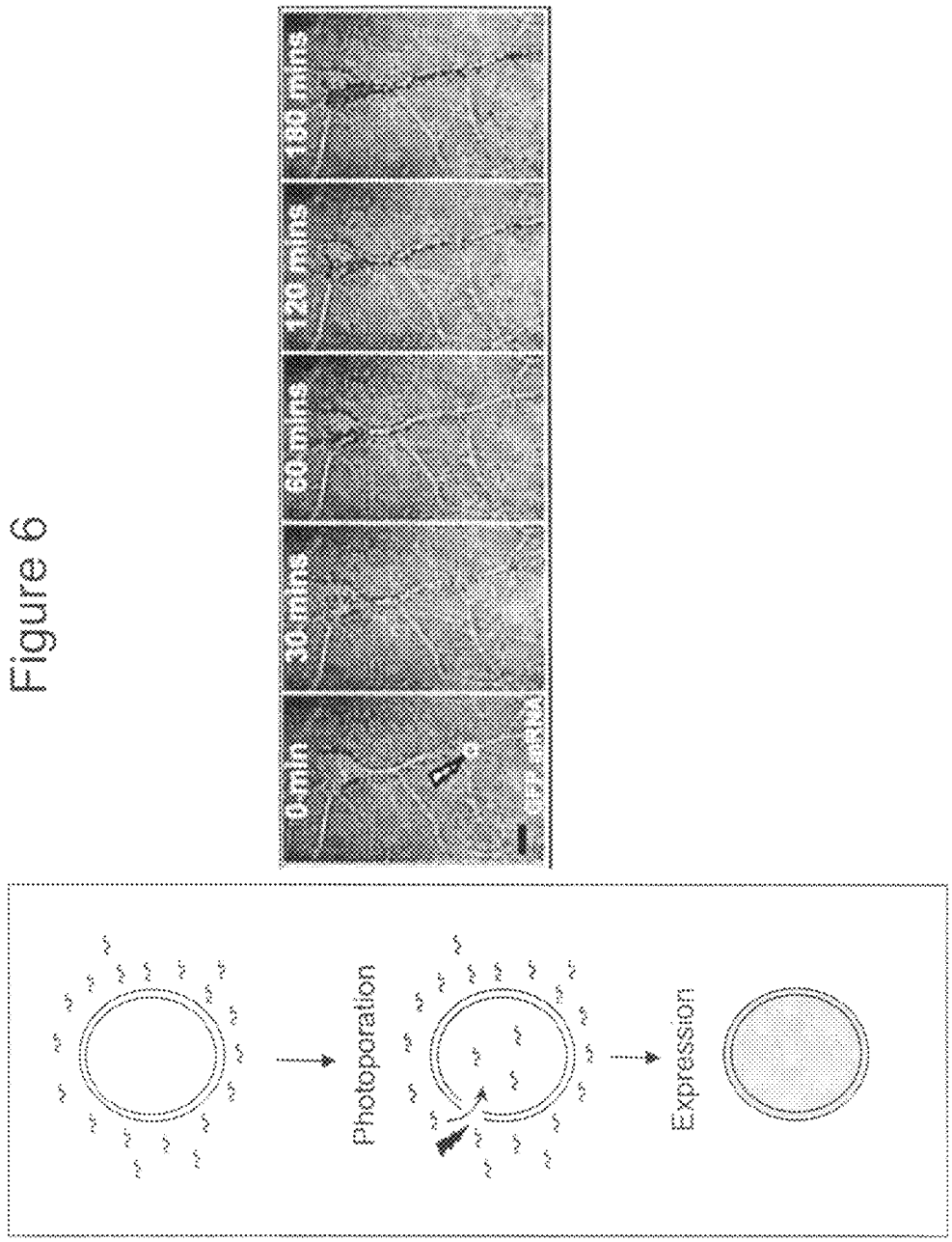
FIG. 6 is a series of images illustrating photoporation of mRNA into neurons. The first image (far left) is a schematic illustration of the photoporation technique. A Ti-sapphire laser was used to temporarily induce small holes in lipid membranes, allowing bath-applied mRNA to enter neurons and subsequently be translated. The next five panels are DIC images of a hippocampal neuron before photoporation and at 30, 60, 120 and 180 minutes after photoporation. The hippocampal neuron in culture was bathed in 10 µg/ml capped GFP mRNA. The boxed outline with lightening symbol roughly outlines the area of photoporation in a distal dendrite; the actual area of photoporation within the boxed region is too small to illustrate. Following photoporation, GFP fluorescence was detected in the neuron. Scale bar=20 µm.

Locally Translated Elk-1 Protein can Initiate Dendrite Degeneration and Produce Cell Death In order to specifically assess the role of dendritically localized Elk, a technique was developed to focally introduce mRNA into distal dendrites of live intact neurons. The technique is similar to, but distinct from, previous work that used a violet diode laser to transfect plasmid DNA for the purpose of creating stable cell lines (Paterson et al., 2005, Optics Express 13: 595-600). The laser-induced cellular poration (or "photoporation") of neurons was customized for the successful introduction of mRNA into cell-attached dendrites, thus facilitating a functional analysis of dendritic protein synthesis in the intact neuron. This technique utilizes a Ti-sapphire laser to induce small temporary holes in lipid membranes (FIG. 6). Using bath application of mRNA, combined with photoporation, mRNA can be introduced into highly specific locations within cells in areas less than 2 µm×2 µm in diameter, without detrimental cellular consequences. Importantly, this technique also allows for the introduction of very small amounts of mRNA through regulation of the concentration of mRNA in the bath solution and through regulation of the laser intensity to modulate the pore size and duration of opening. This feature advantageously facilitates the use of more physiologically relevant changes in protein abundance compared to plasmid DNA transfections, where the amount of protein expression cannot be as directly or reliably controlled. The number of mRNAs that diffuse into a photoporated dendrite can be estimated based upon the following conditions: the concentration of mRNA in the photoporation chamber is 10-15 µg/ml, the volume of the solution is 1 ml and the diffusion coefficient for an RNA of ~1000 bases is 3 square elm/sec. Further, the area that is photoporated is 0.16 square microns for each 5 ms pulse. Thus, approximately 1.2-1.8 molecules of RNA are introduced with each laser pulse. Based on this estimate, and the fact that between 8-16 laser pulses were used for each experiment, between 10 and 30 molecules of RNA, maximally were introduced into the dendrite. This range may be an overestimate for a variety of reasons including the increase in diffusion coefficient (~20×) when the RNA moves from an aqueous solution to the cellular cytoplasm. Given that the process of translation is an endogenous biological amplification, such small amounts of RNA can give rise to physiologically relevant levels of protein. Indeed, using mRNA sequences encoding fluorescent tags, time-courses and locations of translation in live neurons following photoporation of mRNA were determined.

Figures 7A, 7B, 7C, 7D:
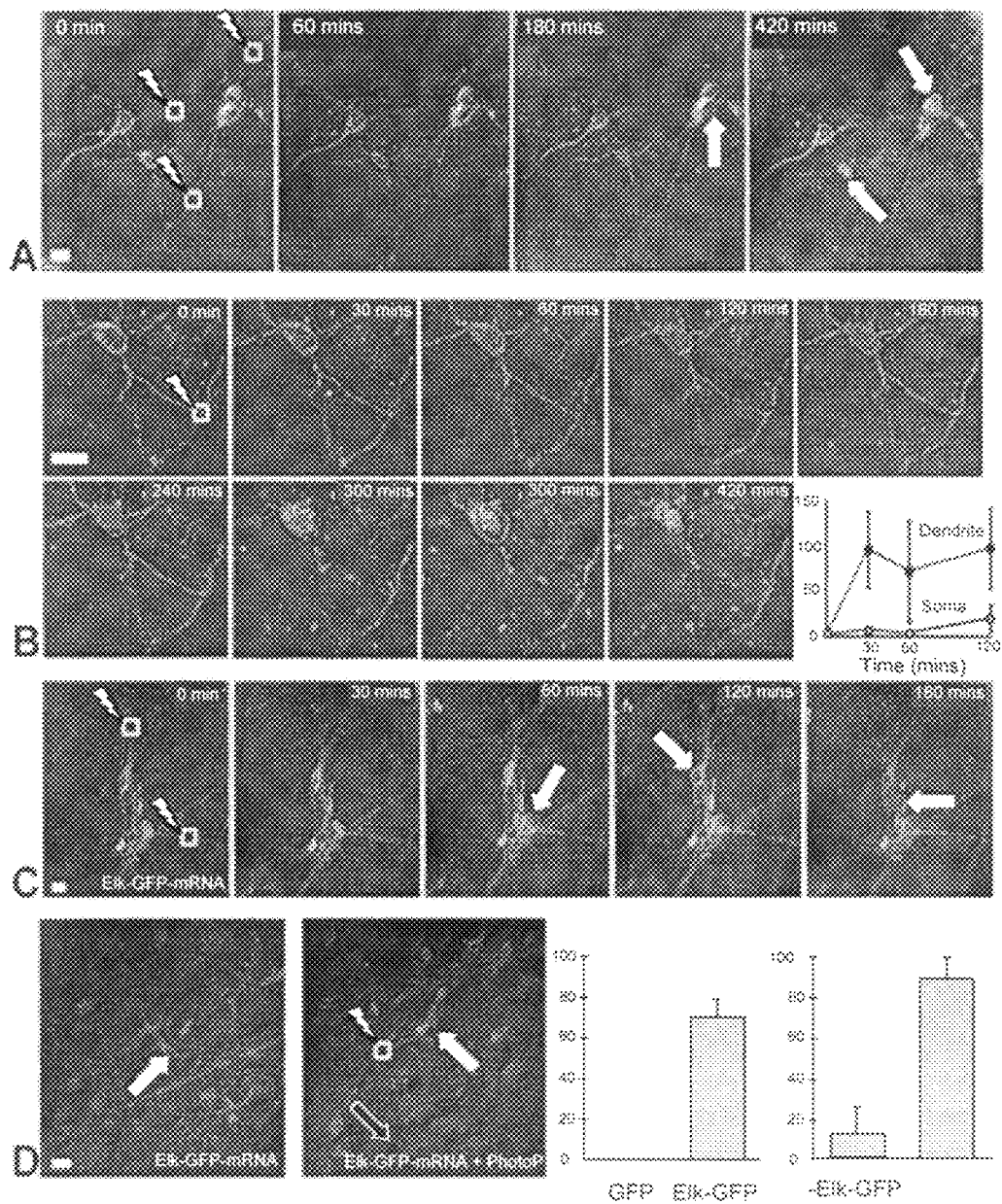
FIG. 7A is a series of DIC images of neurons before photoporation, and at 60, 180 and 420 minutes after photoporation. Elk-1 GFP mRNA was photoporated into distal dendrites in culture. The appearance of cell death and dendrite degeneration (white arrows) follows photoporation.
FIG. 7B is a series of images and a graph. The images depict GFP fluorescence and cell death of a neuron before photoporation, and at 30, 60, 120, 180, 240, 300, 360 and 420 minutes after photoporation. The images are a magnified view of an individual neuron from (A). Scale bar=20 µm. Graph shows the average change in fluorescence intensity over time expressed as a percentage following photoporation of Elk-1 GFP mRNA into distal dendrites (n=3 cells). Open circles show the average change in fluorescence intensity for cell somas and closed circles show the average change in fluorescence intensity for dendrites. Bars represent standard error.
FIG. 7C is a series of DIC images that exhibit neurons before photoporation in culture of Elk-1 GFP mRNA into distal dendrites and at 30, 60, 120 and 180 minutes after photoporation. White arrows indicate the appearance of cell death. Scale bar=20 µm.
FIG. 7D is a series of images and graphs depicting results of a cell viability/cytotoxicity assay. The left image is of neurons bathed in Elk-1 GFP mRNA. The right image is of neurons bathed in Elk-1 GFP mRNA and photoporated. Note the presence of nuclear dye accumulation in the photoporated neuron (white arrow, right image), and the absence of nuclear dye accumulation in the non-photoporated neuron (white arrow, left image). DIC images were taken immediately after photoporation, and overlayed with images showing nuclear dye accumulation taken 3 hours after photoporation. Black arrow shows nuclear dye accumulation in a neighboring astrocyte. The left-hand graph shows the percentage of cells with morphological characteristics of cell death following photoporation with GFP mRNA (n=13 cells) vs. Elk-1 GFP mRNA (n=17 cells). The right-hand graph shows the percentage of cells showing nuclear dye accumulation following photoporation in the absence of Elk-1 mRNA (n=5 cells), compared to photoporation in the presence of Elk-1 mRNA (n=6 cells).
Figure 7E:
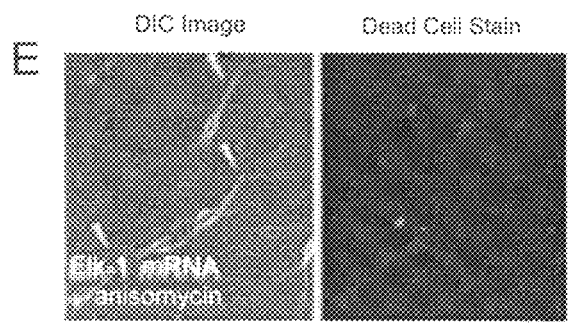
FIG. 7E are images of neurons after photoporation of Elk-1 GFP mRNA in the presence of the translational inhibitor anisomycin. The left image is a DIC image and the right image is a dead cell assay image of neurons following photoporation with Elk-1 GFP mRNA in neurons pre-incubated with anisomycin. Note the absence of cell death following photoporation in the presence of the translational inhibitor.

FIG. 6 shows a cultured hippocampal neuron bathed in an extracellular solution containing GFP-mRNA. Following photoporation of a single dendrite, GFP fluorescence was detected, indicating that the GFP mRNA was successfully introduced into cells and subsequently translated. Note that a significant increase can be seen 30 minutes after photoporation, which is consistent with previous studies using the isolated dendrite transfection/translation assay (Eberwine et al., 2001, Proc. Natl. Acad. Sci. USA 98: 7080-7085; Job and Eberwine 2001b). In the absence of photoporation, no detectable GFP signal was produced, as bath application of mRNA does not promote mRNA entry into neurons (data not shown). After establishing the basic parameters for the photoporation technique, it was used to introduce an Elk-1 mRNA construct containing an in-frame C-terminus GFP sequence tag into dendrites at regions at least 40 µm distal to the cell body (FIG. 7). The appearance of GFP fluorescence after photoporation was used to assess the translation of Elk-1 GFP mRNA and subsequent protein localization. While individual neurons displayed variability in their relative rates of translation and protein trafficking, as expected, GFP fluorescence could be detected 30 minutes after photoporation (FIG. 7B). The appearance of GFP fluorescence was followed by morphological signs of degeneration in dendrites, cytoplasmic swelling, and eventually, cell death (FIGS. 7A, 7B, 7C). The white arrows in FIGS. 7A, 7B and 7C highlight regions of dendrite degeneration and cell death following photoporation of Elk-1 GFP mRNA. Cell death could be visually detected 60 minutes following photoporation of Elk-1 GFP mRNA (FIG. 7C). Pre-incubating neurons with the translational inhibitor, anisomycin, blocked Elk-1-induced cell death (FIG. 7E). This result indicates that translation of the exogenous mRNA, not just the mRNA introduction, is required to produce changes in cell viability.

A cell viability/cytotoxicity assay (Invitrogen Molecular Probes, Carlsbad, Calif.) was used to confirm the morphological observations of cell death following Elk-1 GFP mRNA photoporation. Neurons bathed in Elk-1 GFP mRNA failed to show any nuclear dye accumulation indicative of cell death (FIG. 7D). In contrast, cells photoporated with Elk-1 GFP mRNA produced strong nuclear labeling, confirming the previous finding of cell death following Elk-1 GFP mRNA photoporation (FIG. 7D). Nuclear dye accumulation can be seen in surrounding astrocytes in FIG. 7D (black arrow), as astrocytes can take up nuclear dyes independent of cell death (Arcuino et al., 2002, Proc. Natl. Acad. Sci. USA 99: 9840-9845). Based strictly on morphological observations, 0/13 neurons, photoporated with GFP mRNA, displayed characteristics associated with cell death, whereas 12/17 neurons, photoporated with Elk-1 GFP mRNA, displayed characteristics associated with cell death. Using the cell viability/cytotoxicity assay, only 1/5 neurons, photoporated in the absence of Elk-1 mRNA, displayed nuclear dye accumulation, whereas 5/6 neurons, photoporated in the presence of Elk-1 mRNA, displayed nuclear dye accumulation (FIG. 7D). Obvious morphological signs of cell death may take hours to become apparent, whereas the use of a nuclear dye allows rapid identification of neurons that are in the process of dying. Neurons photoporated with Elk-1 mRNA displayed the same morphology changes and nuclear dye accumulation as neurons photoporated with Elk-1 GFP mRNA, indicating that the addition of a GFP sequence tag was not impacting neuron viability. Photoporation of numerous other mRNAs, including GFP (Clontech), DS-RED (Clontech), Venus-CFP (mutated EYFP cloned in the Haydon lab) and an unrelated *Xenopus* elongation factor 1α (pTRI-Xef; Ambion), failed to produce cell death in the photoporated neurons (data not shown). This result indicates that neither the photoporation technique itself, nor the introduction and translation of exogenous mRNA, were responsible for producing changes in neuron viability. Furthermore, photoporating Elk-1 mRNA into a neuron cell body did not result in neuronal degeneration or death. By using multiple mRNAs, it has been clearly demonstrated that photoporation of Elk-1 mRNA into dendrites is unique in its ability to initiate cell death.

Several pieces of evidence point to locally translated Elk-1 GFP mRNA as the most likely cause of dendrite degeneration and subsequent cell death after photoporation. First, it is unlikely that the Elk-1 GFP mRNA is able to reach the cell body before the initiation of cell death. Studies using [$^3$H]-uridine labeled mRNA to study anterograde transport in cultured hippocampal neurons have estimated the speed of mRNA transport to range around 10-20 µm/hour (Davis et al., 1987, Nature 330: 477-479; Davis et al, 1990, The Journal of Neuroscience 10: 3056-3068; Kleiman et al., 1993, Proc. Natl. Acad. Sci. USA 90: 11192-11196). If one assumes retrograde transport of mRNA to occur at the same rate, Elk-1 GFP mRNA photoporated into dendrites would not reach the cell body before the initiation of cell death, as the sites of photoporation were at least 40 µm from the cell body, and degeneration and cell death began as soon as 60 minutes following photoporation (FIG. 7C). This suggests that the translation of Elk-1 GFP mRNA is occurring in the dendrites, as opposed to the cell body, during the time-course in which cell death is initiated. (Given the small amount of Elk-1 GFP mRNA that is photoporated into dendrites, it is not possible to perform in situ hybridization on the photoporated mRNA.) Second, as shown in FIGS. 6 and 7B, if the Elk-1 GFP mRNA was being made in the cell body, one would expect all processes to show equivalent GFP fluorescence. Instead, the primary GFP signal is seen in the photoporated dendrites, not the surrounding dendrites, again suggesting that local translation is occurring in the photoporated dendrites. Lastly, as shown in the graph of average fluorescence intensity changes over time in FIG. 7B (n=3 cells), the largest increase in GFP fluorescence first appears in dendrites during the time-course in which cell death is initiated. While GFP fluorescence eventually increases in the cell body as well, the appearance of GFP fluorescence in dendrites first, suggests that the Elk-1 GFP mRNA is being translated in dendrites before it reaches the cell body. If Elk-1 GFP mRNA were being transported to the cell body and translated there, one would expect to see the GFP fluorescence in the cell body before the dendrite, yet on average fluorescence is observed in the dendrite before the cell body. This data not only points to local translation of Elk-1 GFP mRNA as the likely initiator of cell death, but it also indicates that the Elk-1 GFP protein may be acting locally in dendrites as well as in the cell body. This is consistent with the finding of dendrite degeneration seen preceding cell death (FIGS. 7B, 7C). The photoporation data is also consistent with the previous findings of cell death and changes in dendrite morphology following whole-cell Elk-1 over-expression (FIGS. 4A, 5A, 5B).

Experimental Example 7

Mitochondrial PTP Function is Necessary for Elk-1 Mediated Cell Death

Given that Elk-1 in dendrites can associate with mitochondria (FIG. 3), and that Elk-1 introduced and translated in dendrites can lead to cell death (FIG. 6), the role of mitochondria in Elk-1 mediated cell death was assessed. Using photoporation, GFP Elk-1 mRNA was introduced into dendrites after pre-incubation with the mitochondrial PTP inhibitor, bongkrekic acid (BKA). Cyclosporin A (CSA), another common PTP inhibitor was not used in this experiment since it also inhibits calcineurin, which has been identified as a primary Elk-1 phosphatase (Sugimoto et al., 1997, J. Biol. Chem. 272:29415-29418). By pre-incubating neurons with BKA, Elk-1 induced cell death was blocked (FIG. 8C), indicating that the Elk-1 cell death pathway is dependent upon mitochondrial PTP function.

Experimental Example 8

Elk-1 Transcriptional Activity is Necessary for Elk-1 Mediated Cell Death

Figure 8A:
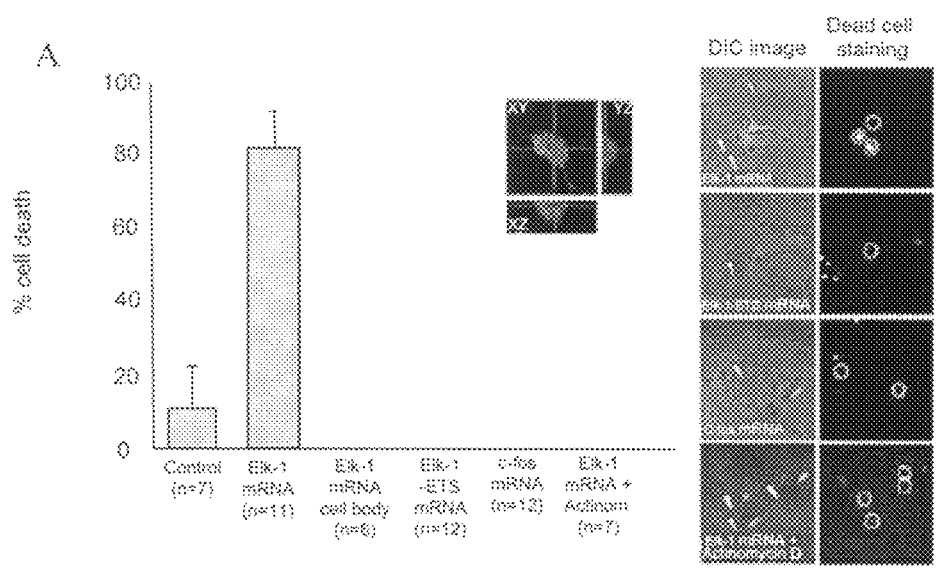
FIG. 8A is a series of a graph and images. The graph depicts the percentage of cells that died following photoporation under a variety of conditions. Control (n=7; photoporation in dendrites without mRNA) Elk-1 mRNA (n=11; photoporation in dendrites with Elk-1 GFP mRNA), Elk-1 mRNA cell body (n=6; photoporation of Elk-1 GFP mRNA into cell bodies), Elk-1-ETS mRNA (n=12; photoporation in dendrites with an Elk-1 construct lacking its DNA binding domain), c-fos mRNA (n=12; photoporation in dendrites with c-fos mRNA), Elk-1 mRNA+ actinomycin D (n=7; photoporation in dendrites with Elk-1

In order to assess whether the cell death associated with dendritically synthesized Elk-1 was transcriptionally dependent, full length Elk-1 GFP mRNA was photoporated into dendrites in the presence of the transcriptional inhibitor actinomycin D. Pre-incubation with actinomycin D inhibited Elk-1 induced cell death (FIG. 8A), indicating that transcriptional activity in general is required for producing cell death. In order to assess whether Elk-1 transcriptional activity specifically was required to produce cell death, an Elk-1 construct lacking its DNA binding domain, Elk-1-ETS, was generated. Photoporation of the Elk-1-ETS mRNA construct into dendrites failed to produce any change in cell viability in contrast to the full-length Elk-1 mRNA construct, indicating that Elk-1 transcriptional activity was required to produce changes in cell viability (FIG. 8A).

These data demonstrate that dendritically synthesized Elk-1 is able to move to the nucleus to impact transcription. In fact, following photoporation of Elk-1 GFP mRNA in dendrites, GFP fluorescence became visible in the cell body and nucleus. In FIG. 6A inset, the cell soma that is shown is from a neuron that had been photoporated in the dendrite with Elk-1 GFP mRNA. The localization of Elk-1 GFP by confocal microscopy permits a 3D viewing of the cell from various visual planes. The orientation of the cell in the visual field is such that the XY plane would be that observed when looking down on the cell while the YZ and XZ planes are the data visualized from the side of the cell. Since Elk-1 GFP fluorescence is observed in all three dimensions throughout the field, these data demonstrate that Elk-1 GFP synthesized from the dendritically-photoporated mRNA is present in the nucleus of the cell. This observation is consistent with the movement of Elk-1 GFP protein to the nucleus where it would be available for subsequent nuclear transcriptional changes.

Figure 8B:
FIG. 8B are images exhibiting Elk-1 GFP mRNA photoporation into cell bodies or photoporation in the absence of Elk-1 GFP mRNA (*) followed by live and dead cell stains. Note the presence of cytoplasmic dye accumulation using the live cell stain (middle image), and the absence of nuclear dye accumulation using the dead cell stain (right panel) indicating that cells did not die following Elk-1 mRNA photoporation into cell bodies.
Figure 8C:
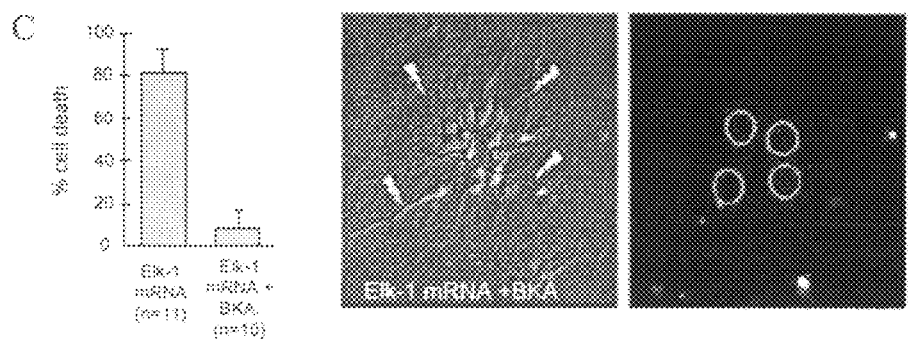
FIG. 8C is a graph and image relating to mitochondrial PTP activity and Elk-1 induced cell death. The graph illustrates the percentage of cells that died following photoporation under the following conditions: Elk-1 mRNA (n=11; photoporation in dendrites with Elk-1 GFP mRNA), and Elk-1 mRNA+BKA (n=10; photoporation in dendrites with Elk-1 GFP mRNA following pre-incubation with the PTP inhibitor, Bongkrekic acid). The middle image depicts neurons photoporated with Elk-1 mRNA+BKA. The right image is of the neurons after dead cell stain and illustrates the absence of nuclear dye accumulation using the dead cell stain indicating that cells did not die following Elk-1 mRNA+BKA photoporation.

Given that the cell death initiated by Elk-1 mRNA translated in dendrites depended on its transcriptional activity, it was of interest to determine whether introduction of Elk-1 mRNA into cell bodies would also produce the same effect. Photoporation of Elk-1 mRNA directly into cell bodies failed to produce cell death (FIGS. 8A and 8B). If Elk-1 mRNA introduced into dendrites was simply transported into the cell body and then translated, one would expect that the same result would be obtained with Elk-1 mRNA introduction directly into the cell body. The results, therefore, indicate that Elk-1 mRNA is capable of producing dramatically different cellular effects when introduced into distinct sub-cellular compartments.

Experimental Example 9

Elk-1 Protein in Diseased Neurons

Given the observation that an over-abundance of Elk-1 can produce dendritic 19 degeneration and decrease cell viability, the presence of Elk-1 in neurons from patients with neurodegenerative diseases was examined.

Figures 9A, 9B, 9C:
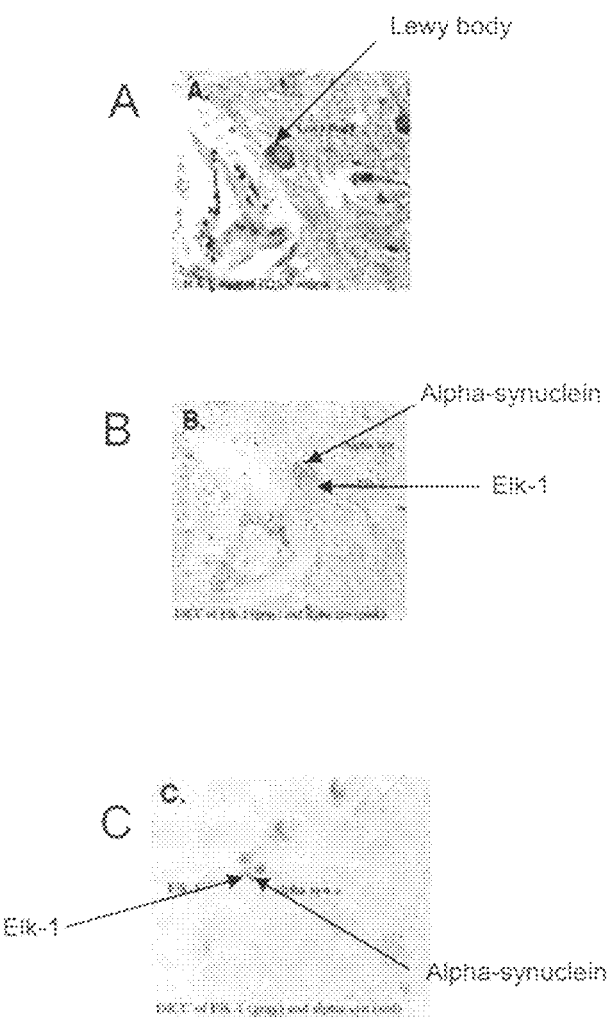
FIG. 9A depicts a neuron containing a Lewy body (indicated by the arrow).
FIG. 9B depicts the same neuron depicted in FIG. 9A and stained with antibodies to alpha-synuclein and Elk-1. The top arrow indicates a region of alpha-synuclein staining in the Lewy body indicated in FIG. 9A. The bottom arrow indicates a region of Elk-1 staining in the Lewy body indicated in FIG. 9A.
FIG. 9C depicts a different neuron stained with anti-alpha-synuclein antibodies and anti-Elk-1 antibodies.

Human tissue sections from patients diagnosed with Parkinson's disease were stained to visualize Lewy bodies (FIG. 9A) and double immunocytochemistry (DICC) stained for alpha-synuclein and Elk-1 (FIGS. 9B and 9C). A clear accumulation of Elk-1 was detected in Lewy bodies in Lewy-body-containing neurons (FIG. 9B). Other neurons in the Parkinson's disease sections were observed to have Elk-1 and alpha-synuclein concentrated in the same neuronal cell (FIG. 9C).

Figure 10A:
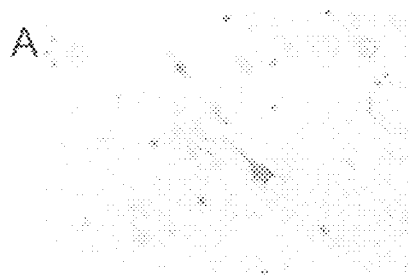
FIGS. 10A and 10B, depicts representative images of stained human tissue obtained from a patient diagnosed with Alzheimer's disease. The section was stained with anti-Elk-1 antibody.
Figure 10B:
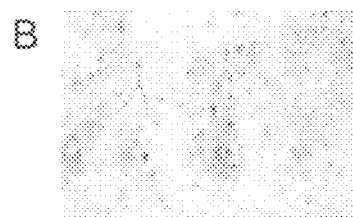

Human tissue sections from patients diagnosed with Alzheimer's disease were stained with anti-Elk-1 antibodies. Elk-1 was detected in both tangle-bearing neurons (FIG. 10A) and in diffuse plaques (FIG. 10B). The image in FIG. 10B is at 10× magnification.

Figure 11A:
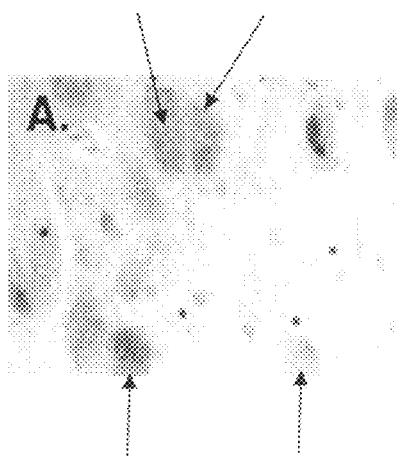
FIGS. 11A and 11B, depicts representative images of stained human tissue obtained from a patient diagnosed with Huntington's disease. The sections were stained to visualize protein aggregates and with anti-Elk-1 antibody.
Figure 11B:
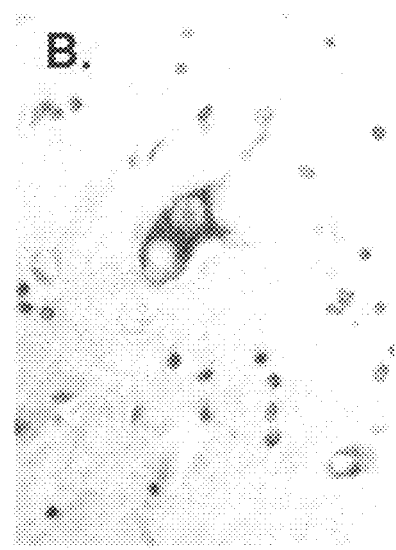

Human tissue sections from patients diagnosed with Huntington's disease were stained to visualize protein aggregates and stained with anti-Elk-1 antibodies to detect Elk-1. Elk-1 was obseved to be concentrated in neurons with protein aggregates (FIG. 11A). A neuron with a large inclusion body and having Elk-1 staining was also detected (FIG. 11B).

These data indicate that there is an increased relative abundance of Elk-1 present in neurons that also contain pathological markers of each of these neurodegenerative diseases. It is believed that this is the first time that a single antigen, Elk-1, has been identified that is associated with the pathological markers in Alzheimer's disease, Parkinson's disease and Huntington's disease.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of increasing competence of a dendrite in need of increased competence, the method comprising decreasing the level of Elk-1 in the dendrite in need of increased competence, wherein decreasing the level of Elk-1 in the dendrite in need of increased competence comprises locally administering an inhibitor of Elk-1 expression to the dendrite in need of increased competence, wherein the inhibitor of Elk-1 expression is an Elk-1 siRNA, and further wherein decreasing the level of Elk-1 in the dendrite in need of increased competence increases competence of the dendrite.

2. The method of claim 1, wherein increasing the competence of a dendrite attached to a neuron leads to increased viability of the neuron.

3. A method of increasing viability of a neuron in need of prolonged viability, the method comprising decreasing the level of Elk-1 in a dendrite attached to the neuron in need of prolonged viability, wherein decreasing the level of Elk-1 in the dendrite attached to the neuron in need of prolonged viability comprises locally administering an inhibitor of Elk-1 expression to the dendrite attached to the neuron in need of prolonged viability, wherein the inhibitor of Elk-1 expression is an Elk-1 siRNA, and further wherein decreasing the level of Elk-1 in the dendrite attached to the neuron in need of prolonged viability increases viability of the neuron.

* * * * *